United States Patent
Del Soldato

(10) Patent No.: US 7,378,412 B2
(45) Date of Patent: May 27, 2008

(54) PHARMACEUTICAL COMPOUNDS

(75) Inventor: Piero Del Soldato, Milan (IT)

(73) Assignee: Nicox S.A., Sophia Antipolis - Valbonne (FR)

(*) Notice: Subject to any disclaimer, the term of this patent is extended or adjusted under 35 U.S.C. 154(b) by 322 days.

(21) Appl. No.: 11/024,857

(22) Filed: Dec. 30, 2004

(65) Prior Publication Data
US 2005/0261242 A1    Nov. 24, 2005

Related U.S. Application Data

(62) Division of application No. 09/926,326, filed as application No. PCT/EP00/03234 on Apr. 11, 2000, now Pat. No. 6,869,974.

(30) Foreign Application Priority Data
Apr. 13, 1999 (IT) .............................. MI99A0753

(51) Int. Cl.
*A01N 43/62* (2006.01)
(52) U.S. Cl. ................. 514/218; 514/252.12; 514/317; 514/277; 540/575; 544/396; 546/241; 546/317
(58) Field of Classification Search ........... 514/218, 514/252.12, 317, 277; 540/575; 544/396; 546/241, 317
See application file for complete search history.

(56) References Cited

U.S. PATENT DOCUMENTS 5,861,426 A    1/1999   Del Soldato et al.
6,869,974 B1*  3/2005   Del Soldato ................ 514/533

FOREIGN PATENT DOCUMENTS

| EP | 0 012 866 A1 | 7/1980 |
| WO | WO 94/12463 | 6/1994 |
| WO | WO 95/09831 | 4/1995 |
| WO | WO 95/30641 | 11/1995 |

OTHER PUBLICATIONS

Pathophysiology: "The Biologic Basis for Disease in Adults and Children", McCance & Huether, 1998, pp. 71-77 and 1025.
K. B. Schwarz, "Oxidative Stress During Viral Infection: A Review", Free Radical Biology & Medicine, vol. 21, No. 5, 1996, pp. 641-649.
F. E. Silverstein et al., "Misoprostol Reduces Serious Gastrointestinal Complications in Patients with Rheumatoid Arthritis Receiving Nonsteroidal Anti-Inflammatory Drugs", Annals of Internal Medicine, vol. 123, No. 4, Aug. 15, 1995, pp. 241-249.
Martindale—The Extra Pharmacopoeia, 31st Edition, 1996, Nonsteriodal Anti-inflammatory Drugs, p. 73.
Current Medical Diagnosis & Treatment 1998, 37th Edition, a Lange Medical Book, pp. 431 and 794.
H. G. Utley et al., "Effect of Sulfhydryl Reagents on Peroxidation in Microsomes", Archives of Biochemistry and Biophysics, vol. 118, 1997, pp. 29-32.
M. S. Nenseter et al., "Paracetamol Inhibits Copper Ion-Induced, Azo Compound-Initiated, and Mono-nuclear Cell-Mediated Oxidative Modificatin of LDL", Atheroscler. Thromb. 15, 1995, pp. 1338-1344.
Brändström et al., "Chemical Reactions of Omeprazole and Omeprazole Analogues", Acta Chemica Scandinavica, vol. 43, 1989, pp. 549-568.
Baylis et al., "Chronic Blockade of Nitric Oxide Synthesis in the Rat Producers Systemic Hypertension and Glomerular Damage", J. Clin. Investigation, vol. 90, 1992, pp. 278-281.
Edwards et al., The Formation of a Structure with the Features of Synovial Lining by Subcutaneous Injection of Air: An In Vivo Tissue Culture System, J. Pathology, vol. 134, 1981, pp. 147-156.

* cited by examiner

Primary Examiner—James O. Wilson
Assistant Examiner—Paul V. Ward
(74) Attorney, Agent, or Firm—Arent Fox LLP

(57) ABSTRACT

Compounds or their salts having general formula:

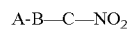

A-B—C—NO$_2$ wherein: A is a drug radical; B is a linker; and C is a bivalent radical.

4 Claims, No Drawings

PHARMACEUTICAL COMPOUNDS

CROSS-REFERENCE TO RELATED APPLICATIONS

This is a Divisional Application of U.S. patent application Ser. No. 09/926,326 filed Oct. 15, 2001, now U.S. Pat. No. 6,869,974, which is a U.S. National Stage entry of International Application Number PCT/EP00/03234 filed Apr. 11, 2000, and which claims priority to Italian Patent Application No. MI99A000753 filed Apr. 13, 1999. The disclosures of the prior applications are hereby incorporated by reference herein in their entirety.

The present invention relates to novel drugs for systemic use and non-systemic use, and the composition thereof, to be used in oxidative stress and/or endothelial dysfunctions cases.

By oxidative stress it is meant the generation of free radicals or radicalic compounds, which causes injury both of the cell and that of the surrounding tissue (Pathophysiology: the biological basis for disease in adults and children, McCance & Huether 1998 pages 48-54).

By endothelial dysfunctions it is meant those relating to the vasal endothelium. The damage of the vasal endothelium is known as one of those important events that can cause a series of pathological processes affecting various organs and body apparatuses, as described hereinafter (Pathophysiology: The biological basis for disease in adults and children, McCance & Huether 1998 page 1025).

As known, the oxidative stress and/or the endothelial dysfunctions are associated to various pathologies as reported hereinafter. The oxidative stress can also be caused by toxicity of a great variety of drugs, which significantly affects their performances.

Said pathological events are of a chronic, debilitating character and are very often typical of the elderly. As already said, in said pathological conditions the drugs used show a remarkably worsened performance.

Examples of pathological situations caused by the oxidative stress and/or by the endothelial dysfunctions, or present in elderly, are the following:

For the cardiovascular system: myocardial and vascular ischaemia in general, hypertension, stroke, arteriosclerosis, etc.

For the connective tissue: rheumatoid arthritis and connected inflammatory diseases, etc.

For the pulmonary system: asthma and connected inflammatory diseases, etc.

For the gastrointestinal system: ulcerative and non-ulcerative dyspepsias, intestinal inflammatory diseases, etc.

For the central nervous system: Alzheimer disease, etc.

For the urogenital system: impotence, incontinence.

For the cutaneous system: eczema, neurodermatitis, acne.

The infective diseases in general (ref.: Schwarz-KB, Brady "Oxidative stress during viral infection: A review" Free radical Biol. Med. 21/5, 641-649 1996).

Further, the ageing process can be considered as a true pathologic condition (ref. Pathophysiology: the biological basis for disease in adults and children, pages 71-77).

The known drugs when administered to patients having pathologies associated to oxidative stress and/or endothelial dysfunctions, show a lower activity and/or higher toxicity.

This happens for example for drugs such as the antiinflammatory, cardiovascular drugs, respiratory apparatus drugs, central nervous system drugs, bone system drugs, antibiotics, urogenital, endocrine drugs, etc.

Drug research is directed to find new molecules having an improved therapeutic index (efficacy/toxicity ratio) or a lower risk/benefit ratio, also for pathological conditions as those above-mentioned, wherein the therapeutic index of a great number of drugs is lowered. In fact, in the above-mentioned conditions of oxidative stress and/or endothelial dysfunctions, many drugs show a lower activity and/or higher toxicity.

For instance, antiinflammatory drugs, such as NSAIDs and anticolitic drugs, such as 5-aminosalicylic acid and its derivatives, show the following drawbacks. NSAIDs result in toxicity particularly when the organism is debilitated or affected by morbid conditions associated to oxidative stress. Said conditions are, for example, the following: age, pre-existing ulcer, pre-existing gastric bleeding, debilitating chronic diseases such as, in particular, those affecting cardiovascular, renal apparatuses, the haematic crasis, etc. ("Misoprostol reduces serious gastrointestinal complications in patients with rheumatoid arthritis receiving non-steroidal anti-inflammatory drugs. A randomized, double blind, placebo-controlled trial." F. E. Silverstein et al., Ann. Intern. Med. 123/4, 241-9, 1995. Martindale 31a ed. 1996, page 73, Current Medical Diagnosis and Treatment 1998, pages 431 and 794).

The administration of anti-infammatory drugs to patients in the above mentioned pathological conditions can be made only at doses lower than those used in therapy in order to avoid remarkable toxicity phenomena. Thus, anti-inflammatory activity results are poor.

Beta-blockers, used for angina, hypertension and cardiac arrhythmia treatment, show side effects towards the respiratory apparatus (dvsploea, bronchoconstriction), and therefore they can cause problems in patients affected by pathologies to said organs (asthma, bronchitis). Therefore, beta-blockers further worsen respiratory diseases such as asthma. Therefore, in asthmatic patients reduced doses of said drugs must be used in order not to jeopardize even more the respiratory functionality. Thus, the efficacy of the beta-blockers results is very reduced.

Antithrombotics, such as, for example, dipyridamole, aspirin, etc., used for the prophylaxis of thrombotic phenomena, have the same drawbacks. In patients affected by pathologies connected to oxidative stress and/or endothelial dysfunctions, the therapeutic action or the tolerability of these drugs, as in the case of aspirin, is greatly reduced.

Bronchodilators, for example, salbutamol, etc., are used in asthma and bronchitis treatment and drugs active on the cholinergic system are used in pathologies such as urinary cholinergic incontinence. Their administration can produce similar side effects affecting the cardiovascular apparatus, causing problems both to cardiopathic and to hypertensive patients. Cardiopathies and hypertension are pathologies associated, as above said, to the oxidative stress and/or endothelial dysfunctions. Also, these drugs show the same drawbacks as those above mentioned.

Expectorant and mucolytic drugs, which are used in the therapy of inflammatory states of the respiratory organs, show drawbacks in patients affected by the above-described conditions. Their administration can give rise to heartburn and gastric irritability, particularly in the elderly.

Bone resorption inhibitors, such as diphosphonates (for example alendronate, etc.) are drugs showing high gastrointestinal toxicity. Therefore, also these drugs can show the same drawbacks as those above mentioned.

Phosphodiesterase inhibitors, such as, for example, sildenafil, zaprinast, used in cardiovascular and respiratory system diseases, are charaterized by similar problems as to tolerability and/or efficacy in the mentioned pathological-conditions of oxidative stress and/or endothelial dysfuntions.

Antiallergic drugs, for example, cetirizine, montelukast, etc. show similar problems in the mentioned pathological conditions, particularly as concerns their efficacy.

Anti-angiotensin drugs, such as ACE-inhibitors, for example, enalapril, captopril, etc., and receptor inhibitors, for example, losartan, etc., are used in cardiovascular disease treatment. Their drawback is side effects to the respiratory apparatus (i.e. cough, etc.) in the above-mentioned pathological conditions.

Antidiabetic drugs, both of the insulin-sensitizing and of hypoglycaemizing type, such as, for example, sulphonylureas, tolbutamide, glypiride, glyclazide, glyburide, nicotinamide etc., are ineffective in the prophylaxis of diabetic complications. Their administration can give side effects, such as, for example, gastric lesions. These phenomena become more intense in the pathological conditions above mentioned.

Antibiotics, for example, ampicillin, clarithromycin, etc., and antiviral drugs, acyclovir, etc., show problems as regards their tolerability, for example, they cause gastrointestinal irritability.

Antitumoral drugs, for example, doxorubicin, daunorubicin, cisplatinum, etc., have high toxicity, towards different organs, among which are stomach and intestine. Said toxicity is further worsened in the above-mentioned pathologies of oxidative stress and/or endothelial dysfunctions.

Antidementia drugs, for example, nicotine and colinomimetics, are characterized by a poor tolerability especially in the above-mentioned pathologies.

The need was felt to have available drugs showing an improved therapeutic performance, i.e., endowed both of a lower toxicity and/or higher efficacy, so that they could be administered to patients in morbid conditions of oxidative stress and/or endothelial dysfunctions, without showing the drawbacks of the drugs of the prior art.

It has now surprisingly and unexpectedly been found that the aforementioned problems evidenced by the administration of drugs to patients affected by oxidative stress and/or endothelial dysfunctions, or to the elderly in general, are solved by a novel class of drugs as described hereinafter.

An object of the invention are compounds or their salts having the following general formulas (I) and (II):

$$A\text{-}B\text{---}C\text{---}N(O)_s \qquad (I)$$

wherein:
s=an integer equal to 1 or 2, preferably s=2;
A=R—$T_1$—, wherein
R is the drug radical and
$T_1$=(CO)$_t$ or (X)$_{t'}$, wherein X=O, S, NR$_{1C}$, R$_{1C}$ is H or a linear or branched alkyl, having from 1 to 5 carbon atoms, or a free valence, t and t' are integers and equal to zero or 1, with the proviso that t=1 when t'=0; t=0 when t'=1;
B=-$T_B$-$X_2$-$T_{B1}$ wherein
$T_B$ and $T_{B1}$ are equal or different;
$T_B$=(CO) when t=0, $T_B$=X when t'=0, X being as above defined;
$T_{B1}$=(CO)$_{tx}$ or (X)$_{txx}$ wherein tx and txx have the 0 or 1 value; with the proviso that tx=1 when txx=0, and tx=0 when txx=1; X is as above defined;
$X_2$ is a bivalent bridging bond as defined below;
C is the bivalent -$T_C$— Y radical, wherein
$T_C$=(CO) when tx=0, $T_C$=X when txx=0, X being as above defined;

Y is an alkylenoxy group R'O wherein R' is linear or branched when possible $C_1$-$C_{20}$, preferably having from 1 to 6 carbon atoms, most preferably 2-4, or a cycloalkylene having from 5 to 7 carbon atoms, in the cycloalkylene ring one or more carbon atoms can be substituted by heteroatoms, the ring may have side chains of R' type, R' being as above defined; or $$\text{---}[\text{C}]_{nIX}\underset{\underset{R_{TIX'}}{|}}{\overset{\overset{R_{TIX}}{|}}{}}\text{---}Y^3\text{---}[\text{C}]_{nIIX}\underset{\underset{R_{TIIX'}}{|}}{\overset{\overset{R_{TIIX}}{|}}{}}\text{---}O\text{---} \qquad (III)$$

wherein:
nIX is an integer between 0 and 3, preferably 1;
nIIX is an integer between 1 and 3, preferably 1;
$R_{TIX}$, $R_{TIX'}$, $R_{TIIX}$, $R_{TIIX'}$, equal to or different from each other are H or a linear or branched $C_1$-$C_4$ alkyl; preferably $R_{TIX}$, $R_{TIX'}$, $R_{TIIX}$, $R_{TIIX'}$ are H.
$Y^3$ is a saturated, unsaturated or aromatic heterocyclic ring containing at least one nitrogen atom, preferably one or two nitrogen atoms, said ring having 5 or 6 atoms.

$$\text{---}(\text{CH}_2)_{n3}\text{---}\underset{}{\bigcirc}\text{---}(\text{CH}_2)_{n3'}\text{---}\text{O}\text{---}$$

wherein n3 is an integer from 0 to 3 and n3' is an integer from 1 to 3;

$$\text{HOOC}\underset{}{\bigcirc}\overset{(\text{CH}_2)_{n3'}\text{---}\text{O}\text{---}}{}(\text{CH}_2)_{n3}\text{---}$$

wherein n3 and n3' have the above mentioned meaning $$(\text{CH}_2\text{---}\underset{\underset{\text{ONO}_2}{|}}{\text{CH}}\text{---}\text{CH}_2\text{---}\text{O})_{nf''}\text{---}$$

$$\text{---}(\text{CH}_2\text{---}\underset{\underset{\text{ONO}_2}{|}}{\text{CH}}\text{---}\text{CH}_2\text{---}\text{O})_{nf''}\text{---}$$

wherein nf' is an integer from 1 to 6 preferably from 1 to 4;

$$(\text{CH}\text{---}\text{CH}_2\text{---}\text{O})_{nf'}\text{---}$$
$$\underset{R_{1f}}{|}$$
$$(\text{CH}_2\text{---}\text{CH}\text{---}\text{O})_{nf'}\text{---}$$
$$\underset{R_{1f}}{|}$$

wherein $R_{1f}$=H, $CH_3$ and nf is an integer from 1 to 6; preferably from 1 to 4;

preferably Y=—R'O— wherein R' is as above defined;
preferably R' is a $C_1$-$C_6$ alkylene;

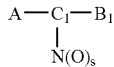
(II)

wherein:

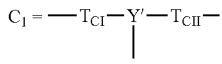

wherein $T_{CI}$ and $T_{CII}$ are equal or different, $T_{CI}$=(CO) when t=0, $T_{CI}$=X when t'=0, X being as above defined;

$T_{CII}$=(CO)$_{tI}$ or (X)$_{tII}$, wherein tI and tII have the 0 or 1 value; with the proviso that tI=1 when tII=0, and tI=0 when tII=1; X is as above defined;

Y' is as Y above defined, but with three free valences instead of two, preferably:

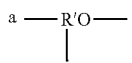

group wherein R' is as above defined,
preferably from 1 to 6 carbon atoms, most preferably 2-4, or

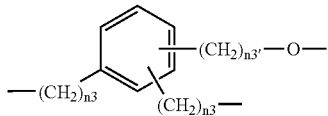

wherein n3 is an integer from 0 to 3 and n3' is an integer from 1 to 3;

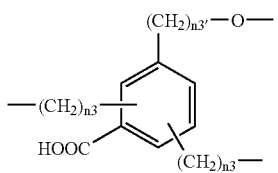

wherein n3 and n3' have the above mentioned meaning;

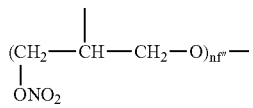

wherein one hydrogen atom on one of the carbon atoms is substituted by a free valence;

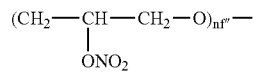

wherein nf is an integer from 1 to 6 preferably from 1 to 4; wherein one hydrogen atom on one of the carbon atoms is substituted by a free valence;

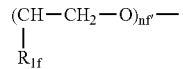

wherein one hydrogen atom on one of the carbon atoms is substituted by a free valence;

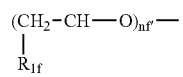

wherein $R_{1f}$=H, $CH_3$ and nf is an integer from 1 to 6; preferably from 1 to 4; wherein one hydrogen atom on one of the carbon atoms is substituted by a free valence;

preferably Y'=—R'O— wherein R' is a linear or branched $C_2$-$C_4$, the oxygen which in Y' is covalently linked to the —N(O)$_S$ group is at the end of the free bond indicated in $C_1$ formula;

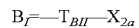

wherein $X_{2a}$ is a monovalent radical as defined below,
$T_{BII}$=(CO) when tI=0, $T_{BII}$=X when tII=0, X being as above defined;

$X_2$, bivalent radical, is such that the corresponding precursor of

B: -$T_B$-$X_2$-$T_{BI}$-meets the test 4, precursor in which the $T_B$ and $T_{BI}$ free valence are each saturated with -OZ, -Z, or with -$Z^I$—N-$Z^{II}$, $Z^I$ and $Z^{II}$ being equal or different and have the Z values as defined below, depending on the fact that $T_B$ and/or $T_{BI}$=CO or X, in connection with, the values of t, t', tx and txx;

$X_{2a}$ monovalent radical, such that the corresponding precursor of $B_I$-$T_{BII}$-$X_{2a}$ meets the test 4, precursor wherein the free valence of $T_{BII}$ is saturated with -OZ, -Z or with —$Z^I$—N-$Z^{II}$, $Z^I$ and $Z^{II}$ being equal or different and having the Z values as defined below, depending on the fact that $T_{BII}$=CO or X, in connection with the values of tI and tII;

the drug A=R-$T_1$-, wherein the free valence is saturated as indicated hereinafter:

when t'=O with:

O-Z wherein Z=H or $R_{1a}$, $R_{1a}$ being a linear or when possible branched $C_1$-$C_{10}$ alkyl, preferably $C_1$-$C_5$, or with -$Z^I$-N-$Z^{II}$, $Z^I$ and $Z^{II}$ being as above defined, when t=0 with -Z, wherein Z is as above defined, with the proviso that the drug is not a steroid, is such to meet at least one of the tests 1-3;

wherein test 1 (NEM) is a test in vivo carried out on four groups of rats (each formed by 10 rats), the controls (two groups and the treated (two groups) of which one group of the controls and one group of the treated respectively are administered with one dose of 25 mg/kg s.c. of N-ethylmaleimide (NEM) the controls being treated with the carrier and the treated groups with the carrier+the drug of formula A=R-$T_1$-, wherein the free, valence is saturated as above indicated, administering the drug at a dose equivalent to the maximum one tolerated by the rats that did not receive NEM, i.e. the highest dose administrable to the animal at which there is no manifest toxicity, i.e. such as to be symptomatologically observable; the drug complies with test 1, i.e., the drug can be used to prepare the compounds of general formula (I) and (II), when the group of rats treated with NEM+carrier+drug shows gastrointestinal damages, or in the group treated with NEM+carrier+drug are observed gastrointestinal damages greater than those of the group treated with the carrier, or of the group treated with the carrier+drug, or of the group treated with the carrier+NEM;

wherein test 2 (CIP) is a test in vitro wherein human endothelial cells from the umbilical vein are harvested under standard conditions, then divided into two groups (each group replicated five times), of which one is treated with a mixture of the drug $10^{-4}$ M concentration in the culture medium, the other group with the carrier; then cumene hydroperoxide (CIP) having a 5 mM concentration in the culture medium is added to each of the two groups; the drug meets test 2, i.e. the drug can be used to prepare the compounds of general formula (I) and (II), if a statistically significant inhibition of the apoptosis (cellular damage) induced by CIP is not obtained with $p<0.01$ with respect to the group treated with the carrier and CIP;

wherein test 3 (L-NAME) is a test in vivo carried out on four groups of rats (each group formed by 10 rats) for 4 weeks and receiving drinking water, the controls (two groups) and the treated (two groups), of which one group of the controls and of the treated, respectively, receives in the above 4 weeks drinking water added of N-co-nitro-L-arginine methyl ester (L-NAME) at a concentration of 400 mg/litre, the controls in the 4 weeks being administered with the carrier and the treated in the 4 weeks with the carrier+the drug, administering the carrier or the drug+carrier once a day, the drug being administered at the maximum dose tolerated by the group of rats not pretreated with L-NAME, i.e., the highest dose administrable to animals at which no manifest toxicity appears, i.e., such as to be symptomatologically observable; after the said 4 weeks, the water supply is stopped for 24 hours and then sacrificed, determining the blood pressure 1 hour before sacrifice, and after sacrifice of the rats determining the plasma glutamic pyruvic transaminase (GPT) after sacrifice, and examining the gastric tissue; the drug meets test 3, i.e., the drug can be used to prepare the compounds of general formula (I) and (II), when in the group of rats treated with L-NAME+carrier+drug, greater hepatic damages (determined as higher values of GPT) and/or gastric and/or cardiovascular damages (determined as higher values of blood-pressure) are found in comparison, respectively, with the group treated with the carrier alone, or with the group treated with the carrier+drug, or with the group treated with the carrier+L-NAME;

the precursors of B or $B_1$ with the free valences saturated as above defined must meet test 4: it is an analytical determination carried out by adding portions of methanol solutions of the precursor of B or $B_1$ at a $10^{-4}$ M concentration, to a methanol solution of DPPH (2,2-diphenyl-1-picryl hydrazyl-free radical); after having maintained the solution at room temperature away from light for 30 minutes, it is read the absorbance at the wavelength of 517 nm of the test solution and of a solution containing only DPPH in the same amount as in the test solution; and then the inhibition induced by the precursor towards the radical production by DPPH is calculated as a percentage by means of the following formula:

$$(1-A_S/A_C) \times 100$$

wherein $A_S$ and $A_C$ are respectively the absorbance values of the solution containing the test compound+DPPH and that of the solution containing only DPPH;

the precursor complies with test 4 when the percentage of inhibition as above defined is equal to or higher than 50%.

Preferably the precursor compound of B or $B_1$ (precursor of the $X_2$ or $X_{2a}$ radical in the formulas (I) and (II), respectively), is selected from the following classes of compounds:

Aminoacids, selected from the following: L-carnosine (formula CI), anserine (CII), selenocysteine (CIII), selenomethionine (CIV), penicillamine (CV), N-acetyl-penicillamine (CVI), cysteine (CVII), N-acetyl-cysteine (CVIII), glutathione (CIX) or its esters, preferably ethyl or isopropyl ester:

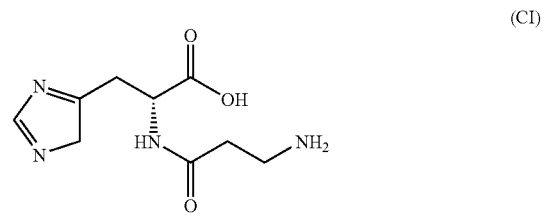

(CI)

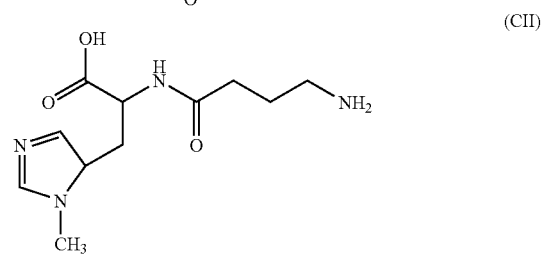

(CII)

(CIII)

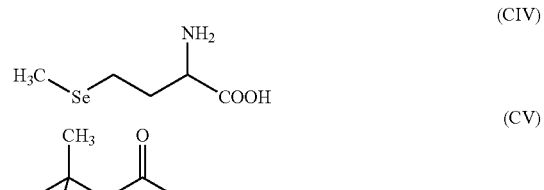

(CIV)

(CV)

(CVI)

(CVII)

(CVIII)

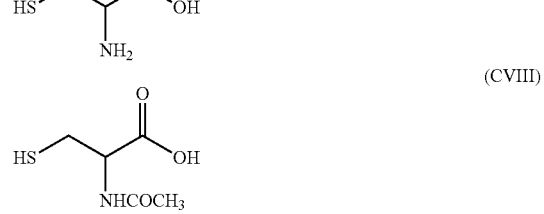

-continued (CIX)
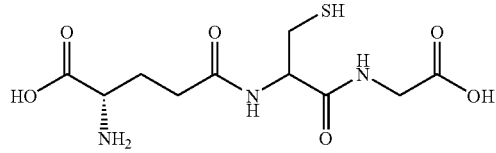

hydroxyacids, selected from the following: gallic acid (formula DI), ferulic acid (DII), gentisic acid (DIII), citric acid (DIV), caffeic acid (DV), hydro caffeic acid (DVI), p-coumaric acid (DVII), vanillic acid (DVIII), chlorogenic acid (DIX), kynurenic acid (DX), syringic acid (DXI):

(DI)
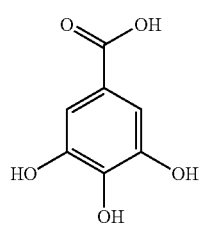

(DII)
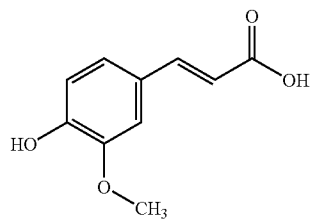

(DIII)
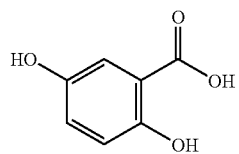

(DIV)
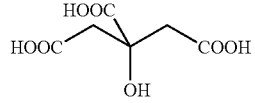

(DV)
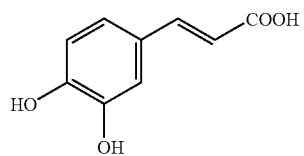

(DVI)
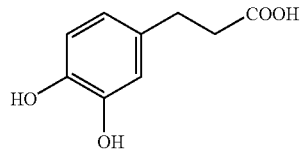

(DVII)
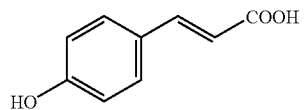

(DVIII)
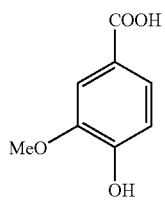

(DIX)
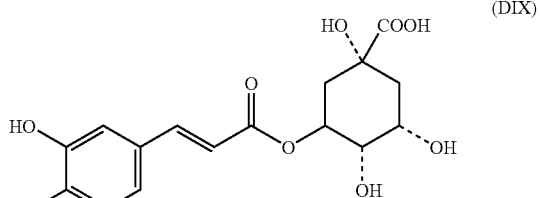

(DX)
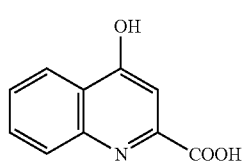

(DXI)
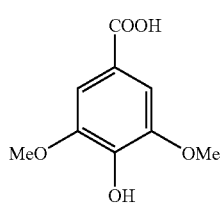

Aromatic and heterocyclic mono- and polyalcohols, selected from the following: nordihydroguaiaretic acid (EI), quercetin (EII), catechin (EIII), kaempferol (EIV), sulphur-ethyne (EV), ascorbic acid (EVI), isoascorbic acid (EVII), hydroquinone (EVIII), gossypol (EIX), reductic acid (EX), methoxyhydroquinone (EXI), hydroxyhydroquinone (EXII), propyl gallate (EXIII), saccharose (EXIV), vitamin E (EXV), vitamin A (EXVI), 8-quinolol (EXVII), 3-ter-butyl-4-hydroxyanisole (EXVIII), 3-hydroxyflavone (EXIX), 3,5-ter-butyl-p-hydroxytoluene (EXX), p-ter-butyl phenol (EXXI), timolol (EXXII), xibornol (EXXIII), 3,5-di-ter-butyl-4-hydroxybenzyl-thio-glycolate (EXXIV), 4'-hydroxybutyranilide (EXXV), guaiacol (EXXVI), tocol- (EXXVII), isoeugenol (EXXVIII), eugenol (EXXIX), piperonyl alcohol (EXXX), allopurinol (EXXXI), conyferyl alcohol (EXXXII), 4-hydroxyphenetyl alcohol (EXXXIII), p-coumaric alcohol (EXXXIV), curcumin (EXXXV):

(EI)
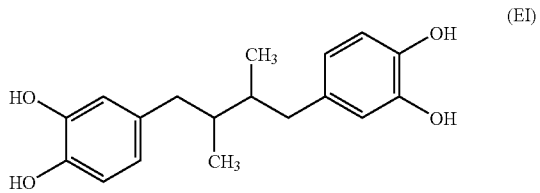

-continued

-continued
(EXVI) 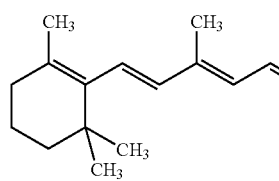
(EXVII) 
(EXVIII) 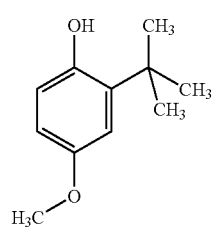
(EXIX) 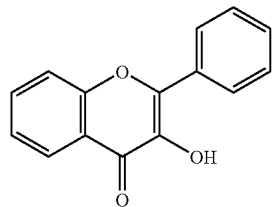
(EXX) 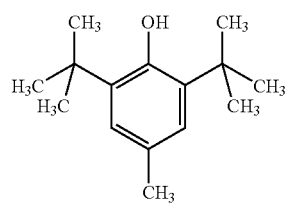
(EXXI) 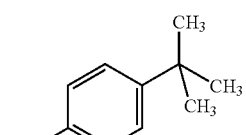
(EXXII) 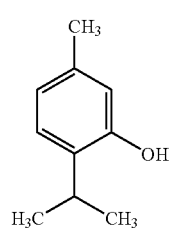
(EXXIII) 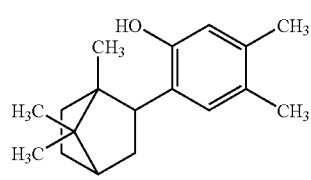
-continued
(EXXIV) 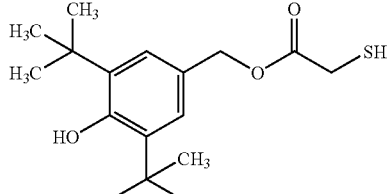
(EXXV) 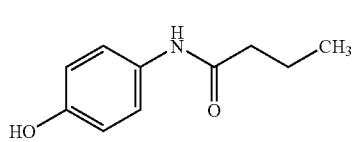
(EXXVI) 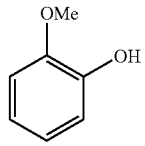
(EXXVII) 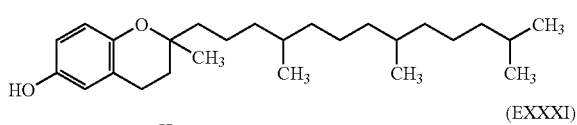
(EXXXI) 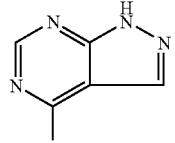
(EXXVIII) 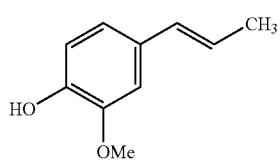
(EXXIX) 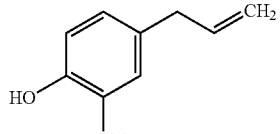
(EXXX) 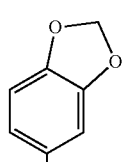
(EXXXII) 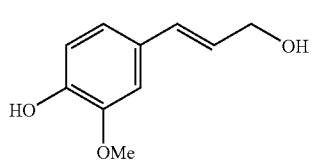
(EXXXIII) 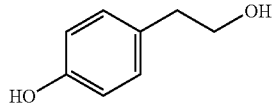

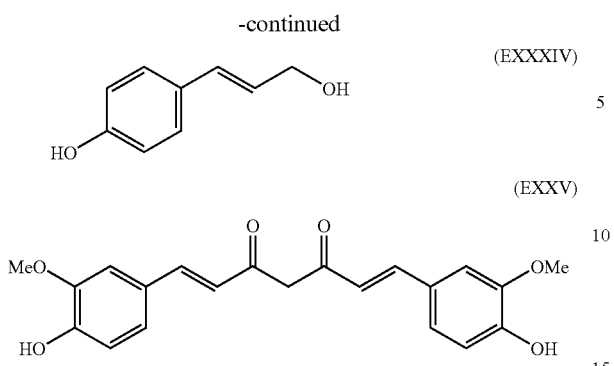

aromatic and heterocyclic amines, selected from the following: N,N'-diphenyl-p-phenylenediamine (MI), ethoxyquin (MII), thionine (MIII), hydroxyrea (MIV):

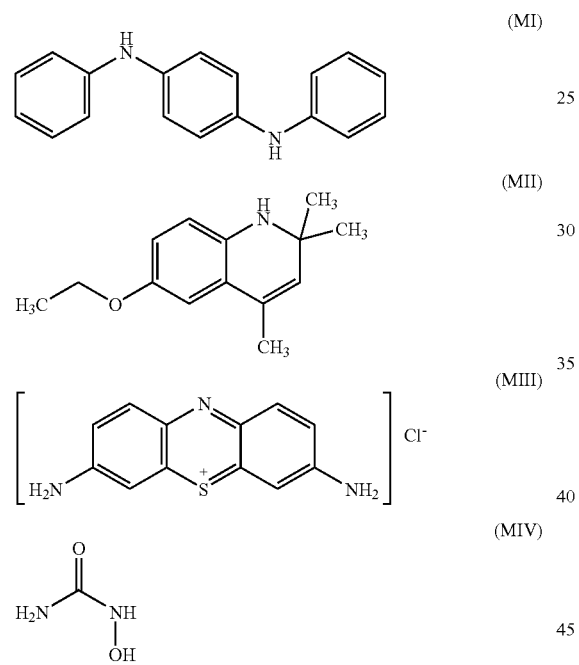

Compounds containing at least a free acid function, selected from the following: 3,3'-thiodipropionic acid (NI), fumaric acid (NII), dihydroxymaleic acid (NIII), thioctic acid (NIV), edetic acid (NV), bilirubin (NVI), 3,4-methylendioxycinnamic acid (NVII), piperonylic acid (NVIII):

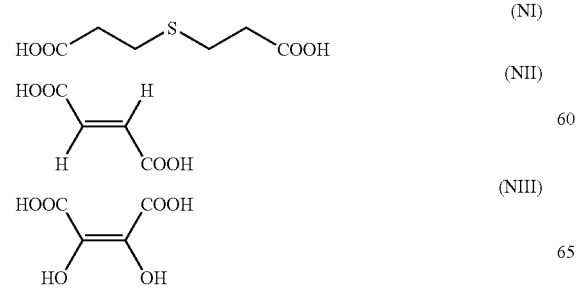

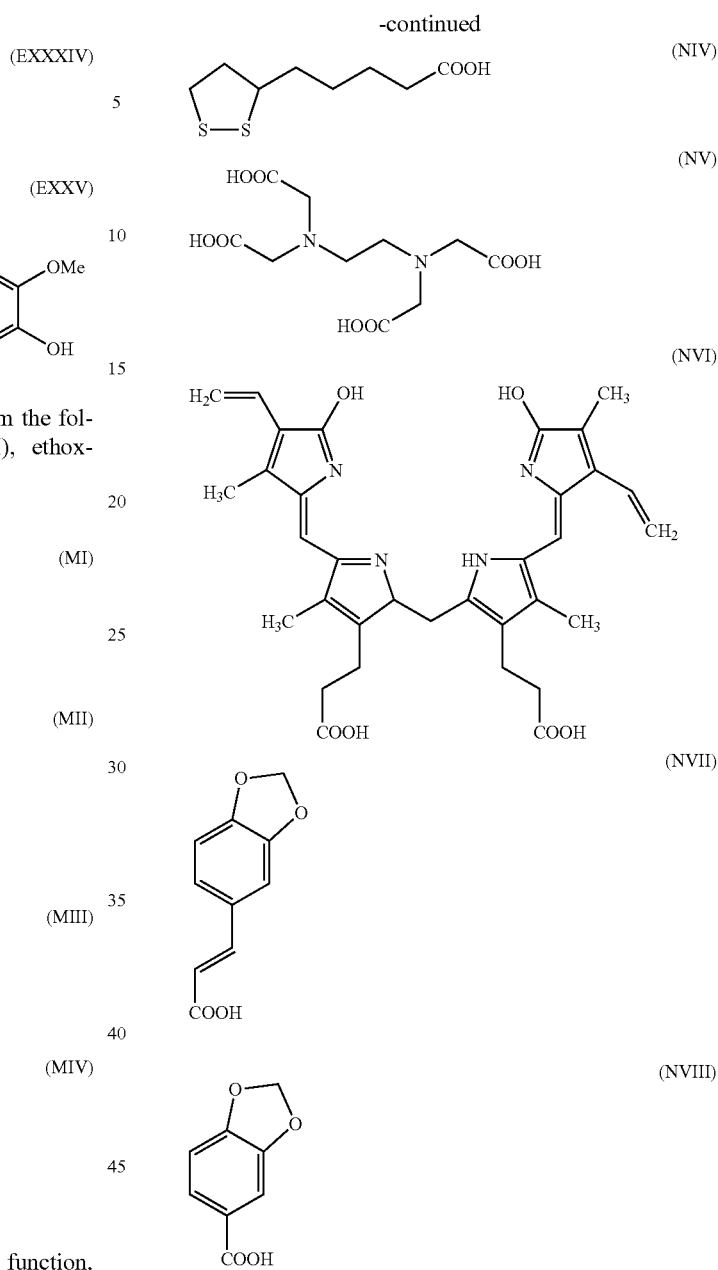

The above-mentioned precursors are prepared according to the known methods in the prior art, for example, described in "The Merck Index," 12a Ed. (1996), herein incorporated by reference. When available, the corresponding isomers and optical isomers can be used.

Tests 1-3 that are carried out for selecting the precursor drug (hereafter indicated in the tests also as "drug") to be used for the synthesis of the products of the invention are in details the following:

Test 1 (NEM): evaluation of the gastrointestinal damage from oxidative stress induced by free radicals formed following administration of N-ethylmaleimide (NEM) (H. G. Utley, F. Bernheim, P. Hochstein "Effects of sulphydril reagents on peroxidation in microsomes" Archiv. Biochem. Biophys. 1118, 29-32 1967).

The animals (rats) are distributed in the following groups (no. 10 animals for group):

A) Control Groups:

1° group: treatment: only carrier (aqueous suspension 1% w/v of carboxymethylcellulose, dose: 5 ml/Kg when the drug is administered by os, or a physiologic solution when parenterally administered, i.e., by subcutaneous, intraperitoneal, intravenous or intermuscular route), 2° group: treatment: carrier as above defined+NEM, B) Groups treated with the drug:

group I: treatment: carrier+drug, group II: treatment: carrier+drug+NEM.

The administration routes are those known for the drug, and can be the oral or subcutaneous, intraperitoneal, intravenous or intramuscular route.

The NEM dose is of 25 mg/kg in physiologic solution (subcutaneous route) and the drug is administered one hour later, in suspension in the carrier, as a single dose which corresponds to the maximum one, or the highest still tolerated by the animals of the group of rats not pretreated with NEM, i.e., the highest administrable dose to said group at which there is no manifest toxicity in the animals, defined as a toxicity that is clearly recognizable for its symptoms. The animals are sacrificed after 24 hours and then one proceeds to the evaluation of the damage to the gastrointestinal mucosa.

The drug meets test 1, i.e., it can be used to prepare the compounds of general formula (I) and (II), when the group of rats treated with NEM+carrier+drug shows gastrointestinal damages, or in said group the gastrointestinal damages noticed are greater than those shown by the group treated with the carrier alone, or the group treated with carrier+drug, or the group treated with carrier+NEM, even though the drug pharmacotherapeutic efficacy, assayed by using specific tests, is not significantly reduced.

Test 2 (CIP): Protection parameter of endothelial cell against the oxidative stress induced by cumene hydroperoxide (CIP).

Human endothelial cells of the umbilical vein are prepared according to a usual standard procedure. Fresh umbilical veins are filled with a 0.1% by weight collagenase solution and incubated at 37° C. for 5 minutes.

Afterwards the veins are perfused with medium M 199 (GIBCO, Grand Island, N.Y.) pH 7.4 further added of other substances, as described in the examples. The cells are collected from the perfusate by centrifugation and harvested in culture flasks T-75, pretreated with human fibronectin. The cells are then harvested in the same medium, further added with 10 ng/ml of bovine hypothalamic growth factor. When the cells of the primary cell culture (i.e., that are directly obtained from ex-vivo) form a single layer of confluent cells (about 8,000,000 cells/flask), the culture is stopped and the layers washed and trypsinized. The cellular suspensions are transferred into the wells of a cell culture plate having 24 wells, half of which is then added with the same culture medium containing the drug at a $10^{-4}$ M concentration, and harvested in a thermostat at 37° C. at constant moisture. Only the cells coming from said first sub-cultures are used for the experiments with cumene hydroperoxide (CIP). The cells are identified as endothelial cells by morphological examination and by their specific immunological reaction towards factor VIII; said cultures did not show any contaminations from myocytes or fibroblasts.

Before starting the test, the cellular culture medium is removed and the cellular layers are carefully washed with a physiologic solution at a temperature of 37° C. The wells of the culture plate are then incubated for one hour with CIP at a 5 mM concentration in the culture medium. The evaluation of cellular damage (apoptosis) is carried out by determining the percent variation of the DNA fragmentation with respect to the control group (treated with CIP alone), evaluating the fluorescence variation at the wavelength of 405-450 nm. 5 replicates for each sample are carried out.

The drug meets the test, i.e., it can be used for preparing the compounds of general formula (I) and (II), when a statistically significant inhibition of apoptosis (cellular damage) induced by CIP with respect to the group treated with CIP alone is not obtained at $p<0.01$.

Test 3 (L-NAME): evaluation of the endothelial dysfunction induced by administration of L-NAME (N'-nitro-L-arginine-methyl ester) J. Clin. Investigation 90, 278-281, 1992.

The endothelial dysfunction is evaluated by determining the damage to the gastrointestinal mucosa, the hepatic damage and blood hypertension induced by administration of L-NAME.

The animals (rats) are divided in groups as herein below shown. The group receiving L-NAME is treated for 4 weeks with said compound dissolved at a concentration of 400 mg/litre in drinking water. The following groups are constituted (No. 10 animals for group):

A) Control Groups:

1° group: only carrier (aqueous suspension 1% w/v of carboxymethylcellulose, dose: 5 ml/Kg when the drug is administered by os, physiologic solution when administered parenterally), 2° group: carrier+L-NAME, B) Groups Administered with the Drug:

3° group: carrier+drug,

4° group: carrier+drug+L-NAME.

The administration routes are those known for the drug, and can be the oral or subcutaneous, intraperitoneal, intravenous or intramuscular route. The drug is administered at that dose which results the highest still tolerated by the animals of the group of rats not pretreated with L-NAME, i.e., the highest administrable dose at which there is no evident toxicity in the animals, i.e. a toxicity recognizable for its symptoms. The drug is administered once a day for 4 weeks.

At the end of the four weeks treatment access to water is prevented and after 24 hours the animals are sacrificed.

One hour before the sacrifice, blood-pressure is determined, and a blood pressure increase is taken as an evaluation of the damage to vascular endothelium. The damage to the gastric mucosa is evaluated as illustrated in test 1 (see example F1). The hepatic damage is determined by evaluation of the glutamic-pyruvic transaminase (GPT increase) after sacrifice.

The drug meets test 3, i.e., it can be used for preparing the compounds of general formula (I) and (II), when in the group of rats treated with L-NAME+drug+carrier it is found an higher hepatic damage (GPT) and/or a higher gastric damage and/or a higher cardiovascular (blood-pressure) damage in comparison to that of the group treated with the carrier alone, or of the group treated with carrier+drug, or of the group treated with carrier+L-NAME; even if the drug pharmacotherapeutic efficacy, assayed by specific tests, is not significantly reduced.

Under the conditions indicated in the above described in vivo tests 1 and 3 the therapeutic index of the drug is reduced since the usual doses at which the drug can be effective are no longer tolerated.

Test 4 is a calorimetric test which affords to establish whether the precursor of B or $B_1$ (precursor of the $X_2$ or $X_{2a}$ of the formulas (I) and (II) respectively), inhibits the production of radicals from DPPH (2,2-diphenyl-1-picryl-hydrazyl) (M. S. Nenseter et al., Atheroscler. Thromb. 15, 1338-1344, 1995). 100 μM solutions in methanol of the tested substances are prepared, and an aliquot of each of said solutions is added to a DPPH solution in methanol 0.1 M. After having stored the solutions at room temperature away from light for 30 minutes, their absorbances are read at the wavelength of 517 nm, together with that of the corresponding DPPH solution at the same concentration. The absorbance decrease with respect to that of the solution of DPPH at the same concentration of the test solutions is determined. The effectiveness of the tested compound in inhibiting formation of radicals by DPPH is expressed by the following formula:

$(1-A_S/A_C) \times 100$ wherein $A_S$ and $A_C$ are respectively the absorbance values of the solution containing the test compound together with DPPH and of the solution containing only DPPH.

The B or $B_1$ precursor satisfies test 4 if their effectiveness in inhibiting radical production as above defined, is equal to or higher than 50% at the indicated concentration ($10^{-4}$ M).

Unexpectedly, the products of the invention of the formulas (I) and (II) in oxidative stress conditions have an improved therapeutic index compared with the precursor drugs.

For illustrative purposes, the above mentioned tests are referred to the following compounds (see the Examples):

Test 1: Precursor Drug: Indomethacin

Maximum administrable dose to rats: 7.5 mg/Kg p.o. By administering a higher dose a toxicity is manifested, characterized by enteropathy, tremor, sedation until death (within 24 hours).

The group of rats treated with NEM+indomethacin at the above mentioned dose shows gastrointestinal damages.

Since indomethacin in the groups treated with NEM causes gastrointestinal damages, it meets test 1. Indomethacin can therefore be used as a drug for preparing the compounds (I) and (II) of the present invention.

Test 2: Precursor Drugs: Indomethacin, Paracetamol and Mesalamine

Indomethacin and paracetamol meet test 2 since the cellular damage (apoptosis) inhibition induced by CIP is not significantly different with respect to that of the controls.

Therefore, the above drugs can be used as drugs for preparing the compounds (I) and (II) of the present invention.

On the contrary, mesalamine does not meet test 2, since it inhibits the apoptosis induced by CIP. Therefore, mesalamine according to test 2 could not be used as a precursor to prepare the compounds (I) and (II) of the present invention. It has been however found that mesalamine submitted to test I causes gastrointestinal damages.

Thus, also, mesalamine can be used as a precursor for preparing the compounds (I) ard (II) of the present invention. Test 3 (L-NAME) precursor drugs: paracetamol, simvastatin, omeprazole.

Paracetamol and simvastatin meet test 3 since they cause gastric and hepatic damages greater than those induced both by L-NAME+carrier and by the drug+carrier.

Therefore, they can be used as precursors to prepare the compounds (I) and (II) of the present invention.

On the contrary, it has been found that omeprazole neither causes gastric nor hepatic damages, nor influences bloodpressure. According to test 3, omeprazole could not be used as a precursor for preparing the compounds (I) and (II) of the present invention.

Test 4 (test for the precursor of B and B, used as bivalent linking bridge): precursor N-acetylcysteine N-acetylcysteine inhibits of 100% the production of radicals induced by DPPH, therefore it meets test 4. Therefore, it can be used as precursor of B or $B_1$.

In formula (III), $Y^3$ is preferably selected from the following:

(Y1)

(Y2)

(Y3)

(Y4)

(Y5)

(Y6)

(Y7)

(Y8)

(Y9)

(Y10)

(Y11)

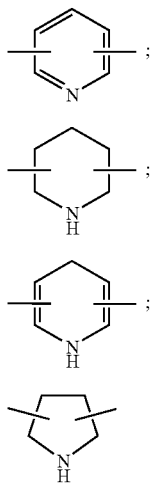

The most preferred of $Y^3$ is Y12 (pyridyl) substituted in positions 2 and 6. The bonds can also be in asymmetric position, for example, Y12 (pyridyl) can be substituted also in position 2 and 3; Y1 (pyrazol) may be 3,5-disubstituted.

The compounds according to the present invention of formula (I) and (II) can be transformed into the corresponding salts. For example, one route to form the salts is the following: when in the molecule one nitrogen atom sufficiently basic to be salified, in organic solvent, such as, for example, acetonitrile, tetrahydrofuran, is present, it is reacted with an equimolecular amount of the corresponding organic or inorganic acid. To form the salt, preferably in the formula of the invention compounds Y or Y' of formula (III) is present.

Examples of organic acids are: oxalic, tartaric, maleic, succinic, citric acids.

Examples of inorganic acids are: nitric, hydrochloric, sulphuric, phosphoric acids.

The derivatives according to the invention can be used in the therapeutic indications of the precursor drug, allowing to obtain the advantages exemplified hereinafter for some groups of these drugs:

Anti-inflammatory drugs NSAIDs: the invention compounds results are very well tolerated and effective, even when the organism is debilitated and is under conditions of oxidative stress. Said drugs can be used also in those pathologies wherein inflammation plays a significant pathogenetic role, such as, for instance, but not limited to, in cancer, asthma, myocardial infarction.

Adrenergic blockers, of α- or β-blocker type: the action spectrum of the compounds of formula (I) and (II) results wider than that of the starting drugs; to a direct action on the smooth musculature the inhibition of the nervous beta-adrenergic signals governing the contraction of the hematic vessels is associated. The side effects (dyspnoea, bronchoconstriction) affecting the respiratory apparatus are lower.

Antithrombotic drugs: the antiplatelet activity is potentiated and in the case of the aspirin derivatives the gastric tolerability is improved.

Bronchodilators and drugs active on the cholinergic system: the side effects affecting the cardiovascular apparatus (tachycardia, hypertension) result lowered.

Expectorants and mucolytic drugs: the gastrointestinal tolerability results improved.

Diphosphonates: the toxicity relating to the gastrointestinal tract is drastically lowered.

Phosphodiesterase (PDE) (bronchodilators) inhibitors: the therapeutic efficacy is improved, the dosage being equal; it is therefore possible, using the compounds of the invention to administer a lower dose of the drug and reduce the side effects.

Anti leukotrienic drugs: better efficacy.

ACE inhibitors: better therapeutic efficacy and lower side effects (dyspnoea, cough) affecting the respiratory apparatus.

Antidiabetic drugs (insulin-sensitizing and hypoglycaemizing) antibiotic, antiviral, antitumoral, anticolitic drugs, drugs for the dementia therapy: better efficacy and/or tolerability.

The drugs which can be used as precursors in formulas (I) and (II) of the compounds of the invention are all those meeting at least one of the above mentioned tests 1, 2, 3. Examples of precursor drugs which can be used are the following:

For anti-inflammatory/analgesic drugs, the following can for example be mentioned:

anti-inflammatory drugs: aceclofenac, acemetacin, acetylsalicylic acid, 5-amino-acetylsalicylic acid, alclofenac, alminoprofen, amfenac, bendazac, bermoprofen, α-bisabolol, bromfenac, bromosaligenin, bucloxic acid, butibufen, carprofen, cinmetacin, clidanac, clopirac, diclofenac sodium, diflunisal, ditazol, enfenamic acid, etodolac, etofenamate, felbinac, fenbufen, fenclozic acid, fendosal, fenoprofen, fentiazac, fepradinol, flufenamic acid, flunixin, flunoxaprofen, flurbiprofen, glucametacin, glycol salicylate, ibuprofen, ibuproxam, indomethacin, indoprofen, isofezolac, isoxepac, isoxicam, ketoprofen, ketorolac, lornoxicam, loxoprofen, meclofenamic acid, mefenamic acid, meloxicam, mesalamine, metiazinic acid, mofezolac, naproxen, niflumic acid, oxaceprol, oxaprozin, oxyphenbutazone, parsalmide, perisoxal, phenyl acetylsalicylate, olsalazine, pyrazolac, piroxicam, pirprofen, pranoprofen, protizinic acid, salacetamide, salicilamide O-acetic acid, salicylsulphuric acid, salsalate, sulindac, suprofen, suxibuzone, tenoxicam, tiaprofenic acid, tiaramide, tinoridine, tolfenamic acid, tolmetin, tropesin, xenbucin, ximoprofen, zaltoprofen, zomepirac, tomoxiprol;

analgesic drugs: acetaminophen, acetaminosalol, aminochlorthenoxazin, acetylsalicylic 2-amino-4-picoline acid, acetylsalicylsalicylic acid, anileridine, benoxaprofen benzylmorphine, 5-bromosalicylic acetate acid, bucetin, buprenorphine, butorphanol, capsaicine, cinchophen, ciramadol, clometacin, clonixin, codeine, desomorphine, dezocine, dihydrocodeine, dihydromorphine, dimepheptanol, dipyrocetyl, eptazocine, ethoxazene, ethylmorphine, eugenol, floctafenine, fosfosal, glafenine, hydrocodone, hydromorphone, hydroxypethidine, ibufenac, p-lactophenetide, levorphanol, meptazinol, metazocine, metopon, morphine, nalbuphine, nicomorphine, norlevorphanol, normorphine, oxycodone, oxymorphone, pentazocine, phenazocine, phenocoll, phenoperidine, phenylbutazone, phenylsalicylate, phenylramidol, salicin, salicylamide, tiorphan, tramadol, diacerein, actarit;

for respiratory and urogenital apparatus drugs (bronchodilators and drugs active on the cholinergic system, expectorants/mucolytics, antiasthmatic/antiallergic antihistaminic drugs), the following can be mentioned:

bronchodilators and drugs active on the cholinergic system: acefylline, albuterol, bambuterol, bamifylline, bevonium methyl sulphate, bitolterol, carbuterol, clenbuterol, chlorprenaline, dioxethedrine, difylline, ephedrine, epinephrine, eprozinol, etafredine, ethylnorepinephrine, etofylline, fenoterol, flutoprium bromide, hexoprenaline, ipratropium bromide, isoetharine, isoprotenerol, mabuterol, metaproterenol, oxybutynin, oxitropium bromide, pirbuterol, procaterol, protokylol, proxyphylline, reproterol, rimiterol, salmeterol, soterenol, terbutaline, 1-teobromineacetic acid, tiotropium bromide, tretoquinol, tulobuterol, zaprinast, cyclodrine, NS-21,2-hydroxy-2,2-diphenyl-N-(1,2,3,6-tetra hydro-pyridin-4-ylmethyl)acetamide;

expectorant/mucolytic drugs: ambroxol, bromhexine, domiodol, erdosteine, guaiacol, guaifenesin, iodinated glycerol, letosteine, mesna, sobrerol, stepronin, terpin, tiopronin; antiasthmatic/antiallergic antihistaminic drugs: acrivastine, alloclamide, amlexanox, cetirizine, clobenzepam, chromoglycate, chromolyn, epinastine, fexofenadine, formoterol, histamine, hydroxyzine, levocabastine, Iodoxamide, mabuterol, metron s, montelukast, nedocromil, repirinast, seratrodast, suplatast tosylate, terfenadine, tiaramide, urushiol, bromhexine; for cardiovascular drugs (ACE-inhibitors, beta-blockers, antithrombotic and vasodilator drugs, antidiabetic and hypoglycemic drugs), the following can be mentioned:

ACE-inhibitors: alacepril, benazepril, captopril, ceronapril, cilazapril, delapril, enalapril, enalaprilat, fosinopril, imidapril, lisinopril, losartan, moveltipril, naphthopidil, perindopril, quinapril, ramipril, spirapril, temocapril, trandolapril, urapidil;

beta-blockers: acebutolol, alprenolol, amosulalol, arotinolol, atenolol, betaxolol, bevantolol, bucumolol, bufetolol, bufuralol, bunitrolol, bupranolol, butofilol, carazolol, carteolol, carvedilol, celiprolol, cetamolol, dilevalol, epanolol, esmolol, indenolol, labetalol, mepindolol, metipranolol, metoprolol, moprolol, nadolol, nadoxolol, nebivolol, nifenalol, nipridalol, oxprenolol, penbutolol, pindolol, practolol, pronethalol, propranolol, sotalol, sulfinalol, talinolol, tertatolol, tilisolol, timolol, toliprolol, xibenolol;

antithrombotic and vasoactive drugs: acetorphan, acetylsalicylic acid, argatroban, bamethan, benfurodil hemisuccinate, benziodarone, betahistine, brovincamine, bufeniode, citicoline, clobenfurol, clopidogrel, cyclandelate, dalteparin, dipyridamole, droprenilamine, enoxaparin, fendiline, ifenprodil, iloprost, indobufen, isbogrel, isoxsuprine, heparin, lamifiban, midrodine, nadroparin, nicotinyl alcohol, nylidrin, ozagrel, perhexiline, phenylpropanolamine, prenylamine, papaveroline, reviparin sodium salt, ridogrel, suloctidil, tinofedrine, tinzaparin, triflusal, xanthinol niacinate;

antidiabetic drugs: acarbose, carbutamide, glibornuride glybuthiazol(e), miglitol, repaglinide, troglitazone, 1-butyl-3-metanyl-urea, tolrestat, nicotinamide;

for antitumor drugs, the following can be mentioned: ancitabine, anthramycin, azacitidine, azaserine, 6-azauridine, bicalutamide, carubicin, carzinophilin, chlorambucil, chlorozotocin, cytarabine, daunorubicin, defosfamide, demecolcine, denopterin, 6-diazo-5-oxo-L-norleucine, docetaxel, doxifluridine, doxorubicin, droloxifene, edatrexate, eflornithine, enocitabine, epirubicin, epitiostanol, etanidazole, etoposide, fenretinide, fludarabine, fluorouracil, gemcitabine, hexestrol, idarubicin, lonidamine, mannomustine, melphalan, menogaril, 6-mercaptopurine, methotrexate, mitobronitol, mitolactol, mitomycins, mitoxantrone, mopidamol, mycophenolic acid, ninopterin, nogalamycin, paclitaxel, pentostatin, pirarubicin, piritrexim, plicamycin, podophyllic acid, porfimer sodium, porfiromycin, propagermanium, puromycin, ranimustine, retinoic acid, roquinimex, streptonigrin, streptozocin, teniposide, tenuazonic acid, thiamiprine, thioguanine, tomudex, topotecan, trimetrexate, tubercidin, ubenimex, vinblastine, vincristine, vindesine, vinorelbine, zorubicin;

for antiulcer drugs the following can be mentioned: F-acetamidocaproic acid, arbaprostil, cetraxate, cimetidine, ecabet, enprostil, esaprazole, irsogladine, misoprostol, omeprazole, ornoprostil, pantoprazole, plaunotol, rioprostil, rosaprostol, rotraxate, sofalcone, trimoprostil;

among anti-hyperlipidemic drugs (statins) the following can be mentioned: atorvastatin, cilastatin, dermostatin, fluvastatin, lovastatin, mevastatin, nystatin, pentostatin, pepstatin, privastatin sodium, simvastatin;

among antibiotic/antiviral drugs the following can be mentioned:

antibiotics: amdinocillin, amoxicillin, ampicillin, apalcillin, apicycline, aspoxicillin, azidamfenicol, azidocillin, azidocillin, aztreonam, benzoylpas, benzyl penicillinic acid, biapenem, bicozamycin, capreomycin, carbenicillin, carindacillin, carumonam, cefaclor, cefadroxil, cefamandole, cefatrizine, cefazedone, cefazolin, cefbuperazone, cefclidin, cefdinir, cefditoren, cefepime, cefetamet, cefixime, cefinenoxime, cefinetazole, cefminox, cefodizime, cefonicid, cefoperazone, ceforamide, cefotaxime, cefotetan, cefotiam, cefoxitin, cefozopran, cefpimizole, cefpiramide, cefpirome, cefprozil, cefroxadine, cefsulodin, ceftazidime, cefteram, ceftezole, ceftibuten, ceftiofur, ceftizoxime, ceftriaxone, cefuroxime, cefuzonam, cephacetrile sodium, cephalexin, cephaloglycin, cephaloridine, cephalosporin C, cephalothin, cephapirin sodium, cephradine, chloramphenicol, chlortetracycline, cinoxacin, clavulanic acid, clometocillin, cloxacillin, cyclacillin, cycloserine, demeclocycline, dicloxacillin, epicillin, fenbecillin, flomoxef, floxacillin, hetacillin, imipenem, lenampicillin, loracarbef, lymecycline, mafenide, meclocycline, meropenem, metampicillin, methacycline, methicillin sodium, meziocillin, minocycline, moxalactam, mupirocin, myxin, negamycin, novobiocin, oxacillin, panipenem, penicillin G potassium salt, penicillin N, penicillin O, penicillin V, phenethicillin potassium salt, pipacycline, piperacillin, pirlimvcin, porfiromvcin, propcillin, quinacillin, ritipenem, rolitetracycline, sancycline, sedecamycin, spectinomycin, sulbactam, sulbenicillin, temocillin, tetracycline, ticarcillin, tiiemonam, tubercidin, azithromycin, clarithromycin, dirithromycin, enviomycin, erythreimycin, josamycin, midecamycin, miokamycin, oleandomycin, rifabutin, rifamide, rifamycin, rifaximin, rokitamycin, spiramycin, troleandromycin, viomycin, virginiamycin;

amikacin, apramycin, arbekacin, dibekacin, dihydrostreptomycin, fortimicins, gentamicin, micronomicin, neomycin, netilmicin, paromomycin, ribostamycin, sisomicin, spectinomycin, streptomicin, tobramycin, trospectomycin;

bacampicillin, cefcapene pivoxil, cefpodoxime proxetil, panipenem, pivampicillin, pivcefalexin, sultamicillin, talampicillin;

carbomycin, clindamycin, lincomycin, mikamycin, rosaramicin, ciprofloxacin, clinafloxacin, difloxacin, enoxacin, enrofloxacin, fleroxacin, flumequine, grepafloxacin, lomefloxacin, nadifloxacin, nalidixic acid, norfloxacin, ofloxacin, pazufloxacin, pefloxacin, pipemidic acid, piromidic acid, rufloxacin, sparfloxacin, tosufloxacin, trovafloxacin, clomocycline, guamecycline, oxytetracycline, nifurpirinol, nifurprazine; p-aminosalicylic acid, p-aminosalicylic acid hydrazide, clofazimine, deoxydihydrostreptomycin, ethambutol, glyconiazide, isoniazid, opiniazide, phenyl aminosalicylate, rifampin, rifapentine, salinazid, 4-4'-sulfynyldianiline, Acediasulfone, dapsone, succisulfone, p-sulfanilylbenzylamine, thiazolsulfone, acetyl sulfamethoxypyrazine, mafenide, 4'-(methylsulfamoyl) sulfanilanilide, salazosulfadimidine, sulfabenzamide, sulfacetamide, sulfachlorpyridazine, sulfachrysoidine, sulfacytine, sulfadiazine, sulfadicramide, sulfadimethoxine, sulfadoxine, sulfaethidole, sulfaguaniidine, sulfaguanole, sulfalene, sulfamerazine, sulfameter, sulfamethazine, sulfamethizole, sulfamethomidine, sulfamethoxazole, sulfamethoxypyridazine, sulfamethylthiazole, sulframetrole, sulfamidochrysoidine, sulfamoxole, sulfanilamide, 2-p-sulfanilylanilinoethanol, N$^4$-sulfanilysulfanilamide, sulfanilylurea, N-sulfanilyl-3,4-xylamide, sulfaperine, sulfaphenazole, sulfaproxyline, sulfapyrazine, sulfapyridine, sulfasomizole, sulfasymazine, sulfathiazole, sulfathiourea, sulfisomidine, sulfisoxazole, 4-sulfanilamido salicylic acid; negamycin, carumonan, cloxyquin, nitroxoline, arginine, metronidazole;

antiviral drugs: acyclovir, amantadine, cidofovir, cytarabine, didanosine, dideoxyadenosine, edoxudine, famciclovir, floxuridine, ganciclovir, idoxuridine, indanavir, kethoxal, lamivudine, MADU, penciclovir, podophyllotoxin, ribavirin, rimantadine, saquinavir, sorivudine, stavudine, trifluridine, valacyclovir, vidarabine, xenazoic acid, zalcitabine, zidovudine; among inhibitors of the bone resorption (diphosphonates) the following can be mentioned: alendronic acid, butedronic acid, etidronic acid, oxidronic acid, pamidronic acid, risedronic acid;

among antidemence drugs the following can be mentioned: arniridine, lazabemide, mofegiline, salbeluzol, oxiracetam, ipidacrine, nebracetam, tacrine, velnacrine.

The preferred substances are the following: among anti-inflammatories: acetylsalicylic acid, 5-aminoacetylsalicylic acid, carprofen, diclofenac sodium, diflunisal, etodolac, flufenamic acid, flunixin, flurbiprofen, ibuprofen, indomethacin, indoprofen, ketoprofen, ketorolac, lornoxicam, loxoprofen, meclofenamic acid, mefenamic acid, meloxicam, mesalamine, naproxen, niflumic acid, olsalazine, piroxicam, salsalate, sulindac, suprofen, tenoxicam, tiaprofenic acid, tolfenamic acid, tolmetin, zomepirac, tomoxiprol;

among analgesic drugs: acetaminophen, acetylsalicylsaliylic acid, benoxaprofen, buprenorphine, butorphanol, capsaicin, diacereine, dihydrocodeine, ethylmorphine, eugenol, phenylbutazone, meptazinol, morphine, nalbuphine, pentazocine, thiorphan, tramadol, actarit;

among respiratory and urogenital apparatus drugs: (bronchodilators, drugs active on the cholinergic system, expectorants/mucolytics, antiasthmatics/antiallergic antihistaminic drugs): bronchodilators and drugs active on the cholinergic system: albuterol, carbuterol, clenbuterol, difhylline, etofylline, fenoterol, ipratropium bromide, metaproterenol, oxybutynin, pirbuterol, salmeterol, terbutaline, tiotropium bromide, zaprinast, cyclodrine, NS-21,2-hydroxy-2,2-diphenyl-N-(1,2,3,6-tetrahydro-pyridin-4-ylmethyl)acetamide;

expectorant/mucolytic drugs: ambroxol, bromexine, guaiacol, sobrerol;

antiasthmatic/antiallergic antihistaminic drugs: cetirizine, chromoglycate, histamine, levocabastine, Iodoxamide, montelukast, terfenadine, bromexine;

among cardiovascular drugs:

ACE-inhibitors: captopril, enalapril, lisinopril, losartan, ramipril;

Beta blockers: alprenolol, atenolol, bupranolol, labetalol, metipranolol, metoprolol, pindolol, propranolol, timolol; antithrombotic and vasoactive drugs: acetylsalicylic acid, acetorphan, argatroban, clopidogrel, dalterarin, dipyridamole, enoxaparin, heparin, iloprost, midodrine, ozagrel, phenylpropanolamine, trifusal;

antidiabetic drugs: tolrestat, nicotinamide;

among antitumor drugs: anthramycin, daunorubicin, doxorubicin, epirubicin, fluorouracyl, methotrexate, vinblastine;

among antiulcer drugs: cimetidine, omeprazole, pantoprazole;

among antihyperlipidemic drugs: lovastatin, pravastatin sodium, simvastatin;

among antibiotic/antiviral drugs:

antibiotic drugs: amoxicillin, ampicillin, aztreonam, biapenem, carbenecillin, cefaclor, cefadroxil, cefamandole, cefatrizine, cefoxitin, clavulanic acid, dicloxacillin, imipenem, meclocycline, methacycline, moxalactam, panipenerm, sulbactam, azithromycin, erythromycin, josamycin, miokamycin, rifabutine, rifamide, rifamycin, gentamicin, paromomycin, sisomicin, bacampicillin, carbomycin, clindamycin, ciprofloxacin, clinafloxacin, difloxacin, enrofloxacin, lomefloxacin, nadifloxacin, norfloxacin, ofloxacin, pipemidic acid, apicycline, clomocycline, oxytetracycline, nifurpirinol, nifurprazine, isoniazid, rifampin, rifapentine, dapsone, thiazolsulfone, sulfamethoxazole, sulfamoxole, metronidazole, arginine;

antiviral drugs: acyclovir, famciclovir, ganciclovir, penciclovir, ribavirin, vidarabine, zidovudine;

among inhibitors of the bone reabsorption: alendronic acid, etidronic acid, pamidronic acid;

among antidemence drugs: oxiracetam, tacrine, velnacrine.

The above-mentioned substances, precursor drugs, are prepared according to the methods known in the prior art. See, for example, in "The Merck Index, 12a Ed. (1996), herein incorporated by reference. When available, the corresponding isomers, comprising optical isomers, can be used.

Tomoxiprol is obtained according to the method described in EP 12,866.

The compounds of formula (I) or (II) are prepared with synthesis methods mentioned below.

The choice of the reactions for each method depends on the reactive groups present in the precursor drug molecule, in the precursor compound of B or B$_I$, which can be, as above mentioned, bivalent or monovalent, and in the precursor compound of C.

The reactions are carried out with methods well known in the prior art, which allow to obtain bonds among the precursor drug, the precursor drug of B or B$_I$ and the precursor compound of C as above defined.

When the reactive function of the precursor drug (for example —COOH, —OH) is involved in a covalent bond, for example, of ester, amide, ether type, said function can be restored with the methods well known in the prior art.

Some synthesis schemes for obtaining the compounds of the invention are reported hereinafter:

A) Synthesis of the Compounds of FormuLa (I).

1. Synthesis of the compound obtained by reaction between the precursor drug and the compound precursor of B.

1a. When the drug has general formula R—COOH and the functional group of the precursor compound of B which binds itself to the drug carboxylic function has the formula XZ, X being as above defined and Z=H, the reactions which take place depend on the nature of the second reactive group present in the precursor compound of B.

1a.1 When the second reactive group present in the precursor compound of B is a carboxylic group, the synthesis general scheme expects the initial formation of the halide of the R—CO-Hal acid (Hal=—Cl, —Br) and the subsequent reaction with the HX group of the precursor compound of B:

(IA.1)

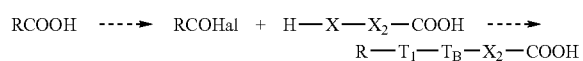

$X_2$, $T_1$, $T_3$ being as above defined.

When in the two reaction compounds other functional groups —COOH and/or HX are present, they must be protected before the reaction according to the methods known in the art; for example, as described in the volume by Th. W. Greene: "Protective groups in organic synthesis", Harvard University Press, 1980.

The RCOHal acylhalide is prepared according to the methods known in the prior art, for example by thionyl or oxalyl chloride, pill or pv halides in inert solvents under the reaction conditions, such as, for example, toluene, chloroform, DMF, etc.

Specifically, if the HX group of the precursor compound of B is $NH_2$, or OH or SH, the precursor drug of formula R-COOH is first converted into the corresponding acyl halide RCOHal, as above mentioned, and then reacted with the HX group of the precursor compound of B in the presence of an organic base, such as triethylamine, pyridine, etc., using an inert solvent in the reaction conditions such as toluene, tetrahydrofuran, etc., at a temperature in the range 0° C.-25° C.

Alternatively to the previous synthesis, the precursor drug of formula R—COOH can be treated with an agent activating the carboxyl group selected from N,N'-carbonyldiimidazol (CDI), N-hydroxybenzotriazol and dicyclohexylcarbodiimide in solvent, such as, for example, DMF, THF, chloroform etc., at a temperature in the range −5° C.-50° C. and the obtained compound reacted in situ with the reactive function of the precursor compound of B for obtaining the compound of formula (IA.1).

1a.2 When the precursor compound of B contains two functional groups XZ, equal to or different from each other, X being as above defined and Z=H, the precursor drug having formula R-COOH is first treated with an agent activating the carboxyl group, as above described in 1a.1, and then with the precursor compound of B, after having protected one of the two reactive HX groups, for example, with acetyl or ter-butyloxycarbonyl, restoring the initial function at the synthesis end. The scheme is the following:

(IA.2)

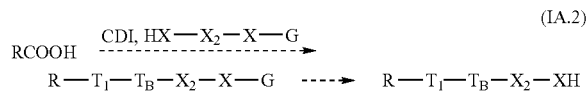

wherein X, $T_1$, $T_B$, $X_2$ are as above defined and G is a protective group of the HX function.

2. Nitroxyderivative synthesis.

2a.1 When the compound obtained at the end of the previous step 1a. has formula (IA.1), the acid can be converted into the corresponding sodic salt and then one can follow the known prior art methods for preparing the final compound, for example according to one of the following synthesis schemes:

(IA.1b)

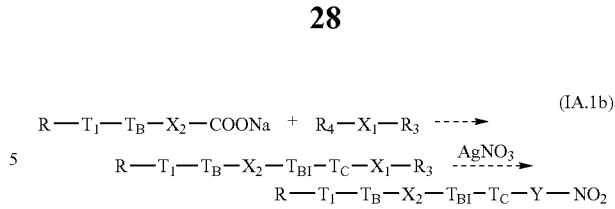

wherein $T_1$, $T_3$, $X_2$, $T_{B1}$, $T_C$ are as above defined, $R_4$ is selected from Cl, Br, Y is as above defined, $X_1$ is the Y radical free from the oxygen atom, $R_3$ is Cl, Br, Iodine, OH. If $R_3$=OH the compound of formula (1A.1b) is subjected to halogenation, for example, with $PBr_3$, $PCl_5$, $SOCl_2$ $PPh_3+I_2$, and then reacted with $AgNO_3$ in organic solvent such as acetonitrile, tetrahydrofuran. If $R_3$ is Cl, Br, Iodine, the compound of formula (1A.1b) is directly reacted with $AgNO_3$ as above mentioned.

(IA.1c)

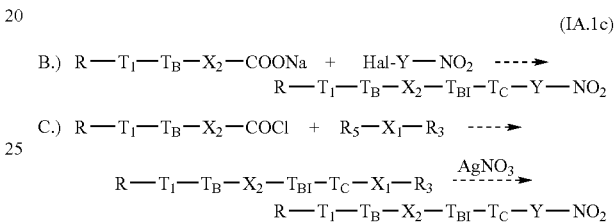

wherein $R_5$=OH or $NHR_{1C}$, $R_{1C}$, $R_3$ and the other symbols being as above defined.

The above shown reactions are well-known in the prior art. See, for example, the patent applications in the name of the Applicant WO 94/12463, WO 95/09831 and WO 95/30641. When $X_1$ is a linear $C_4$ alkyl, the corresponding acid $R—T_1-T_3-X_2$-COOH is reacted with triphenylphosphine in the presence of a halogenating agent such as $CBr_4$ or N-bromosuccinimide in tetrahydrofuran obtaining the compound (1A.1 c) wherein $R_3$=Br.

2a.2 When the compound obtained at the end of the previous step 1a has formula (IA.2), the corresponding nitroxyderivative is obtained by treating a halogen-carboxylic acid of formula Hal-$X_1$—COOH, $X_1$ being as above defined, first with an agent activating the carboxyl group as described in IA.1, and then with the compound of formula (IA.2), obtaining an halogen derivative, which is isolated and then dissolved in organic solvent, (ref. paragraph 2a.1), and treated with silver nitrate. The global reaction scheme is the following:

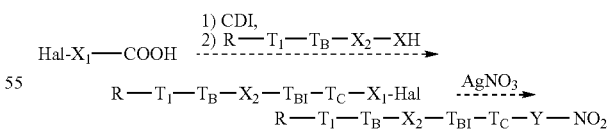

wherein $T_1$, $T_B$, $X_2$, $T_{B1}$, $T_C$, Y are as above defined.

Alternatively, the halide Hal-X, —COCl can be used, wherein Hal is preferably bromine, which is let react with the compound of formula (IA.2).

1b. When the drug precursor has the reactive function HX, wherein X is as above defined, instead of a carboxylic group, the two functional groups present on the precursor compound of B can be the following.

1b.1 A carboxylic group, which reacts with the HX function of the drug precursor, and a HX group, the latter reactive group of the precursor compound of B being equal to or different from the functional group of the drug precursor. The formula of the precursor compound of B is of the H—X—$X_2$—COOH type, wherein X and $X_2$ are as above defined. The H—X— function of the precursor compound of B is protected according to the known prior art methods and the carboxyl group is reacted, as above mentioned, according to the following scheme:

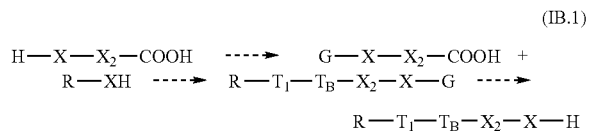
(IB.1)

At the end of the reaction the HX function of the precursor compound of B is restored.

1b.2 When the precursor compound of B contains two carboxylic groups, it is treated with an equimolar amount of an agent activating the carboxyl group under the conditions previously described in 1a.1, and then reacted with the reactive HX function of the drug precursor molecule. Possible other reactive functions of HX type present in the two compounds must be protected as previously mentioned. Lastly, a compound of formula R—$T_1$—$T_B$—$X_2$—COOH (1B.2) is obtained.

2b. Nitroxyderivative synthesis.

2b.1 To obtain the final nitroxyderivative starting from the compound of formula R-$T_1$-$T_B$-$X_2$—X—H (1B.1), obtained at the end of the synthesis described in 1b.1, the (1B.1) compound is reacted with a halogenacid of formula Hal-$X_1$—COOH which has been treated as previously described in paragraph 1a.1, or with the corresponding halogenacid chloride. The resulting compound is dissolved in organic solvent, for example, acetonitrile or tetrahydrofuran, and reacted with silver nitrate.

2b.2 To obtain the final nitroxyderivative starting from the compound of formula R—$T_1$—$T_B$—$X_2$—COOH (1B.2), obtained at the end of the synthesis described in 1b.2, the acid is transformed into the corresponding sodic salt, it is reacted with a $R_4$—$X_1$—$R_3$ compound, previously defined in the reaction A. scheme of paragraph 2a.1, obtaining, according to the same process therein mentioned, the final nitroxyderivative. Alternatively, when $X_1$ is a linear $C_4$ alkyl, the acid (1B.2) is reacted with triphenyl-phosphine in the presence of a halogenating agent such as $CBr_4$ or N-bromosuccinimide in tetrahydrofuran and the resulting compound dissolved in organic solvent, for example, acetonitrile, tetrahydrofuran, is reacted with silver nitrate.

2b.3 Alternatively to the synthesis process according to 1b.1 and 2b.1, it is possible to react in a first step the HX-function of the precursor compound of B HX—$X_2$—COOH with the acyl chloride of an halogenacid of formula Hal-$X_1$—CO—Cl, wherein Hal is preferably Br, and subsequently, the carboxylic function of the so obtained compound, with the drug precursor R—HX. In the third and last step, the -Hal group is substituted with —$ONO_2$ according to the process described in 2b.1. The reaction scheme is the following:

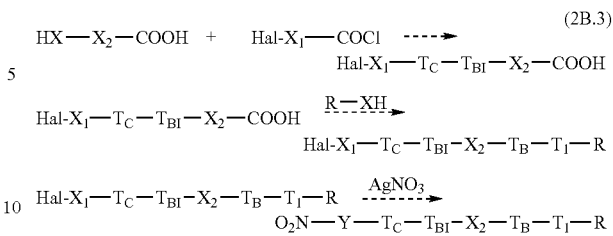
(2B.3)

wherein $T_C$, $T_{B1}$, $T_B$, $T_1$, $X_2$, $X_1$, Y are as above defined. In the previous scheme, the nitration can alternatively be carried out on the acid compound of formula (2B.3).

B) Synthesis of compounds of formula (II).

1 a. When the drug precursor is of formula R-COOH and the precursor compound of B, contains only one functional reactive group of formula XH, X being as above defined, R—COOH is initially converted into the corresponding acylhalide, or treated with an agent activating the carboxyl group as described in 1a.1, and then reacted with the HX function of an halogen-acid compound, said function being equal to or different from that present on the precursor compound of $B_1$, said halogen-acid having the formula:

(IIA.1)

wherein $X_1'$ is Y' as above defined without the oxygen atom through which the —$NO_2$ group is linked, X and Hal are as above defined.

The compound (IIA.1) can be obtained with the known method of the prior art. For example, when X=NH, it can be obtained from the corresponding hydroxy-aminoacid, protecting the aminic group by the corresponding ter-butyloxycarbonyl derivative and transforming the hydroxyl function into halogen group as described for the halogenation of the compound (1A.1b) in 2a.1. The free carboxylic function of the compound resulting from the reaction with the molecule of the drug precursor is reacted with the function present in the molecule of the precursor compound of $B_1$, as previously illustrated in 1a.1 for the reaction between the R—COOH acid and the precursor compound of B. In the final step, the halogen atom (Hal) present on the radical $X'_1$ is substituted with an $ONO_2$ group by adding $AgNO_3$ to an organic solution of the compound. The reaction scheme is the following, exemplified starting from the RCOCl acid halide:

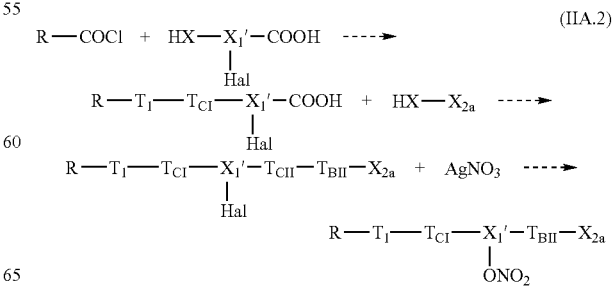
(IIA.2)

1b. When the drug precursor and the precursor compound of $B_1$ contain each a reactive group of general formula XH, the two groups in each of the two molecules being equal to or different from each other, wherein X is as above defined, the synthesis is carried out starting from an halogenacid compound of formula

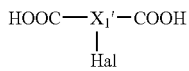

$X_1'$ being as above defined, said compound being prepared from the corresponding hydroxy-diacid as described for the halogenation of the compound (1A.1b) in 2a.1. The halogendiacid compound is treated with an equimolar amount of an agent activating the carboxyl group, under the conditions previously described in 1a.1., and then it is reacted with the reactive function of the drug precursor molecule. In the subsequent step, the second carboxylic function is treated with an activating agent, as previously made for the first, and reacted with the precursor compound of B, according to the following scheme:

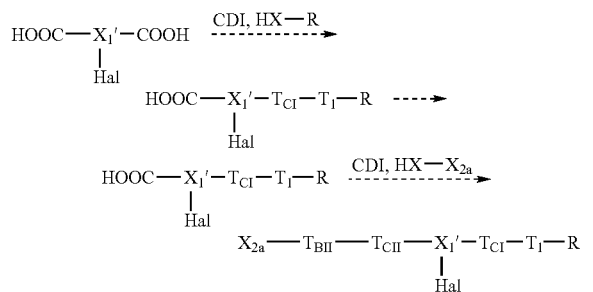

The halogen atom is then substituted with the $ONO_2$ group as above mentioned.

3. Synthesis of the nitroso (s=1) derivatives of formula (I).

3a.1 The compound of formula (1A.1b) wherein $R_3$=OH is reacted with sodium nitrite in a solvent formed of a mixture of water with tetrahydrofuran in the presence of hydrochloric acid. The reaction is widely illustrated in the prior art. The general scheme is the following:

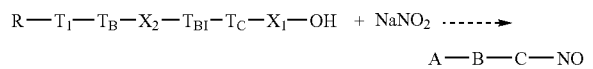

3a.2 If the compound obtained at the end of step A in 1a.2 has formula (IA.2), the corresponding nitroso derivative is obtained treating an hydroxyacid of formula HO—$X_1$—COOH, $X_1$ being as above defined, first with an agent activating the carboxyl group, as described in 1a.1, then reacting it with 1A.2 and the resulting product with sodium nitrite as described in 3a.1.

3b.1 To obtain the nitroso derivative starting from the compound of formula R—$T_1$-$T_B$-$X_2$—XH (1B.1) obtained at the end of the synthesis described in 1b.1, the compound (1B.1) is reacted with an hydroxyacid as described in 3a.2.

3b.2 To obtain the nitroso derivative from the compound of formula R-$T_1$-$T_B$-$X_2$—COOH (1B.2) obtained at the end of the synthesis described in 1b.2, the acid is transformed into the sodic salt and reacted with a compound Hal-$X_1$—OH, as previously described, and the obtained alcohol is treated as described in 3a.1.

4) Synthesis of the Nitroso Derivatives of formula (II)

4a.1 When the drug is of formula R-COOH and the precursor compound of $B_1$ contains only one function reactive group of formula XH, X being as above defined, R—COOH is initially converted into the corrsponding acylhalide or treated with an agent activating the carboxyl group as describied in 1a.1, and then reacted with the HX function of an hydroxy-acid compound, said function being equal to or different from that present on the precursor compound of $B_1$, said hydroxy-acid having the formula:

wherein $X_1'$ is Y' as above defined without the oxygen atom through which the —NO group is linked, X is as above defined.

The free carboxylic function of the compound resulting from the reaction with the drug molecule is reacted with the function present in the molecule of the precursor compound of $B_1$, as previously illustrated in 1a.1 for the reaction between the R—COOH acid and the precursor compound of B. In the final step, the alcohol is transformed into the nitroso-derivative as described in 3a.1.

The reaction scheme is the following, exemplified starting from the RCOCl acid halide:

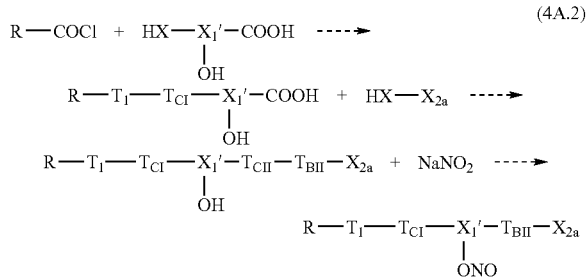

4b. When the drug and the precursor compound of B, contain each a reactive group of general formula XH, the two groups in each of the two molecules being equal to or different from each other, wherein X is as above defined, the synthesis is carried out starting from an hydroxydiacid compound of formula

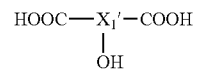

$X_1'$ being as above defined, said hydroxydiacid compound is treated with an equimolar amount of an agent activating the carboxyl group, under the conditions previously described in 1a.1., and then it is reacted with the reactive function of the drug molecule. In the subsequent step, the second carboxylic function is treated with an activating agent, as previously made for the first one, and reacted with the precursor compound of $B_1$ according to the following scheme:

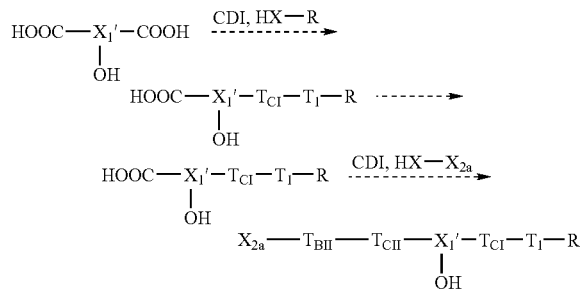

The obtained compound is reacted as described in 3a.1.

The compound objects of the present invention are formulated in the corresponding pharmaceutical compositions for parenteral, oral and topic use according to the well-known methods in the art, together with the usual excipients; see, for example, the volume "Remington's Pharmaceutical Sciences 15a Ed."

The amount on molar basis of the active principle in these formulations is the same, or lower, in comparison with that used of the corresponding precursor drug.

The daily administrable doses are those of the precursor drugs, or in the case lower. The daily doses can be found in the publications of the field, such as, for example, in "Physician's Desk Reference".

The following examples have the purpose to illustrate the invention and are not to be considered as limitative of the same.

EXAMPLE 1

Synthesis of (S,S)-N-acetyl-S-(6-methoxy-x-methyl-2-naphthalen acetyl)cisteine 4-(nitroxy)butyl ester (NCX 2101) having Formula

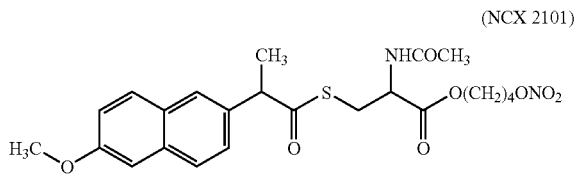

The precursor is naproxene (Formula VI), the precursor of B is N-acetylcisteine (formula CVIII)

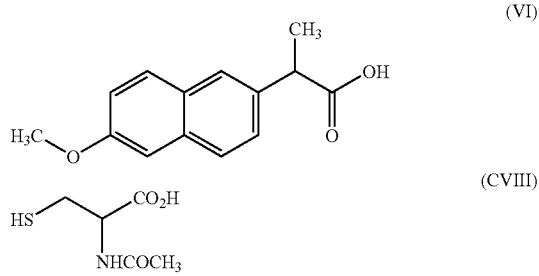

a) Synthesis of (S,S)-N-acetyl-S-(6-methoxy-α-methyl-2-naphthalen acetyl)cisteine To a solution of 6-methoxy-α-methyl-2-naphthalenacetic acid (10 g, 43.4 mmoles) in chloroform (100 ml) and N,N-dimethylformamide (6 ml), 1,1'-carbonyldiimidazole (CDI) (7.04 g, 43.4 mmoles) is added. After 15 minutes, the obtained solution is treated with (S)-N-acetylcisteine (7.08 g, 43.4 mmoles) and left at room temperature for 12 hours. The reaction mixture is washed with HCl 5%, then with water and lastly with brine. The organic phase is anhydrified with sodium sulphate and then evaporated at reduced pressure. The obtained residue is purified by chromatography on silica gel eluting with ethyl acetate. 11.66 g of the expected product in the form of a white solid m.p. 122°-126° C., is obtained.

$^1$H-NMR (CDCl$_3$): 7.71-7.65 (3H, m), 7.34 (1H, dd), 7.16-7.09 (2H, m), 6.36 (1H, d), 4.67 (1H, m), 4.00 (1H, q), 3.90 (3H, s) 3.32 (2H, t), 1.84 (3H, s), 1.59 (3H, d).

b) Synthesis of (S,S)-N-acetyl-S-(6-methoxy-α-methyl-2-naphthalen acetyl)cisteine 4-(bromobutyl) ester To a solution of (S,S)-N-acetyl-S-(6-methoxy-α-methyl-2-naphthalenacetyl)cisteine (11.3 g, 30.1 mmoles) in tetrahydrofuran (200 ml), triphenylphosphine (23.7 g, 90.3 mmoles) and carbon tetrabromide (28.85 g, 90.3 mmoles) are added. The reaction mixture is left under stirring for 24 hours at room temperature. The solvent is removed by evaporation at reduced pressure. The obtained crude product is purified by chromatography on silica gel eluting with n-hexane/ethyl acetate 7/3.4 g of the ester in the form of a white solid with m.p. 67°-71° C., are obtained.

c) Synthesis of (S,S)-N-acetyl-S-(6-methoxy-x-methyl-2-naphthalen acetyl)cisteine 4-(nitroxy)butyl ester To a solution of the ester obtained at the end of the previous step (1 g, 1.96 mmoles) in acetonitrile (20 ml), silver nitrate (0.66 g, 3.92 mmoles) is added. The reaction mixture is heated for 7 hours under reflux away from light. The formed salt is removed by filtration and the solution is evaporated at reduced pressure. The obtained residue is purified by chromatography on silica gel eluting with n-hexane-/ethyl acetate 7/3. 0.47 g of (S,S)-N-acetyl-S-(6-methoxy-α-methyl-2-naphthalenacetyl)cisteine 4-(nitroxy)butyl ester in the form of a white solid m.p. 56-59° C., are obtained.

$^1$H-NMR (CDCl$_3$): 7.80-7.68 (3H, m), 7.37 (1H, d), 7.20-7.13 (2H, m), 6.12 (1H, d) 4.40 (2H, dd), 4.26 (1H, m), 4.15-3.87 (3H, m), 3.92 (3H, s), 2.33 (2H, d) 1.86 (3H, d), 1.74-1.67 (4H, m), 1.61 (3H, d).

Elementary analysis:

| | | | | |
|---|---|---|---|---|
| Calculated | C: 56.08% | H: 5.73% | N: 5.71% | S: 6.51% |
| Found | C: 55.99% | H: 5.68% | N: 5.60% | S: 6.35% |

EXAMPLE 2

Synthesis of (S)-N-acetyl-S-(α-methyl[4-(2-methyl-propyl) benzene]acetyl)cisteine 4-(nitroxy)butyl ester (NCX 2111) having Formula

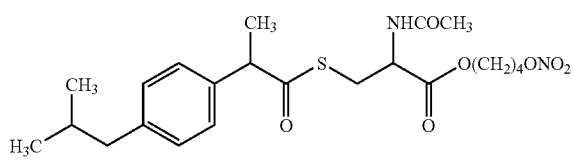

(NCX 2111)

The precursor is ibuprofen (Formula VII), the precursor of B is N-acetylcisteine (formula CVIII)

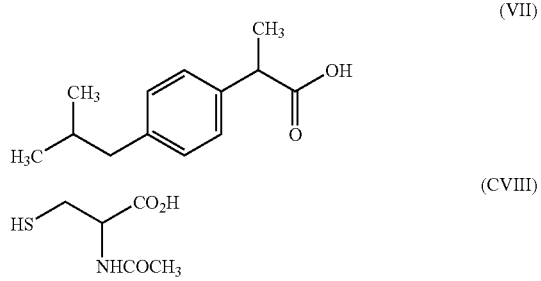

a) Synthesis of (S)-N-acetyl-S-{α-methyl[4-(2-methyl-propyl)benzene]acetyl}cisteine To a solution of α-methyl[4-(2-methylpropyl)benzene] acetic acid (10 g, 48.48 mmoles) in chloroform (100 ml) and N,N-dimethylformamide (6 ml) 1,1'-carbonyldiimidazole (7.86 g, 48.48 mmoles) is added. After 1 hour, the obtained solution is treated with (S)-N-acetylcisteine (7.91 g, 48.47 mmoles) and left at room temperature for 24 hours. The reaction mixture is washed with HCl 5%, then with water and lastly with brine. The organic phase is anhydrified with sodium sulphate and then evaporated at reduced pressure. The obtained residue is purified by chromatography on silica gel eluting with ethyl acetate. 13.3 g of the expected product in the form of an oil are obtained.

$^1$H-NMR (CDCl$_3$): 10.17 (1H, s) 7.13 (2H, d) 6.54 (1H, d), 4.76 (1H, m), 3.93 (1H, q), 3.42-3.30 (2H, m), 2.49 (2H, d), 1.85-1.83 (4H, m), 1.55 (3H, d), 0.93 (6H, d).

b) Synthesis of (S)-N-acetyl-S-[α-methyl[4-(2-methyl-propyl)-benzene]acetyl}cisteine 4-(bromobutyl) ester To a solution of (S)-N-acetyl-S-(α-methyl[4-(2-methyl-propyl)benzene]acetyl}cisteine (12.8 g, 36.4 mmoles) in tetrahydrofuran (100 ml), triphenylphosphine (28.65 g, 109.23 mmoles) and carbon tetrabromide (36.23 g, 109.23 mmoles) are added. The reaction mixture is let under stirring for 48 hours at room temperature. The solvent is removed by evaporation at reduced pressure. The crude product is purified by chromatography on silica gel eluting with cyclohexane/ethyl acetate 1/1.5.79 g of the ester in the form of an oil are obtained.

c) Synthesis of (S)-N-acetyl-S-(α-methyl[4-(2-methyl-propyl) benzene]acetyl}cisteine 4-(nitroxy)butyl ester To a solution of the ester obtained at the end of the previous step (5.5 g, 11.3 mmoles) in acetonitrile (100 ml) silver nitrate (2.69 g, 15.8 mmoles) is added. The reaction mixture is heated for 24 hours under reflux away from light. The formed salt is removed by filtration and the solution is evaporated at reduced pressure. The obtained residue is purified by chomatography on silica gel eluting with cyclohexane/ethyl acetate 7/3. 1.18 g of (S)-N-acetyl-S-{α-methyl[4-(2-methylpropyl)benzene]acetyl}cisteine 4-(nitroxy) butyl ester in the form of an oil are obtained.

$^1$H-NMR (CDCl$_3$): 7.27-7.09 (4H, m), 6.19 (1H, d), 4.75 (1H, m), 4.47 (2H, t), 4.15-4.02 (2H, m), 3.86 (1H, q), 3.31 (2H, d), 2.44 (2H, d), 1.89 (3H, d), 1.86-1.76 (5H, m), 1.51 (3H, d), 0.89 (6H, d).

Elementary analysis:

| | | | | |
|---|---|---|---|---|
| Calculated | C: 56.39% | H: 6.88% | N: 6.00% | S: 6.84% |
| Found | C: 56.22% | H: 6.79% | N: 5.88% | S: 6.92% |

EXAMPLE 3

Synthesis of (S)-N-acetyl-S-[1-(4-chlorobenzoyl)-5-methoxy-2-methyl-1H-indol-3-acetyl]cisteine 4-(nitroxy)butyl ester (NCX 2121) having Formula

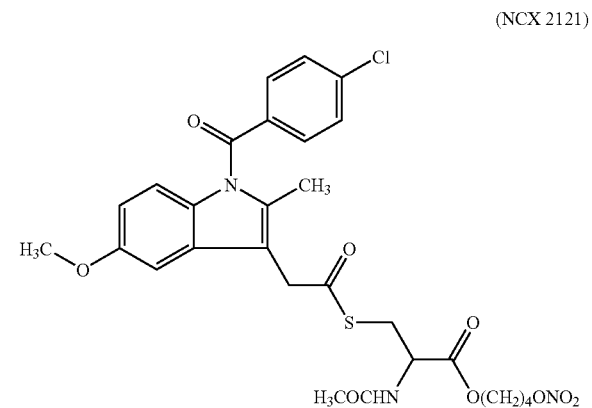

(NCX 2121)

The precursor is indomethacin (Formula VIII), the precursor of B is N-acetylcisteine (formula CVIII)

(VIII)

(CVIII)

a) Synthesis of (S)-N-acetyl-S-[1-(4-chlorobenzoyl)-5-methoxy-2-methyl-1H-indol-3-acetyl]cisteine To a solution of 1-(4-chlorobenzoyl)-5-methoxy-2-methyl-1H-indol-3-acetic acid (10 g, 28.00 mmoles) in chloroform (100 ml) and N,N-dimethylformamide (2 ml) 1,1'-carbonyldiimidazole (4.53 g, 28.00 mmoles) is added. After 1 hour, the obtained solution is treated with (S)-N-acetylcisteine (4.56 g, 28.00 mmoles) and left at room temperature for 24 hours. The reaction mixture is washed with HCl 5%, then with water and lastly with brine. The organic phase is anhydrified with sodium sulphate and then evaporated at reduced pressure. The obtained residue is purified by chromatography on silica gel eluting with ethyl acetate. 7.79 g of the expected product in the form of a yellow solid m.p. 129° C., are obtained.

$^1$H-NMR (DMSO-$d_6$): 12.90 (1H, s), 8.21 (1H, d), 7.69-7.64 (4H, m), 7.06 (1H, d), 6.96 (1H, d), 6.73 (1H, dd), 4.33 (1H, m), 4.02 (2H, s), 3.77 (3H, s), 3.33-2.96 (2H, m), 2.22 (3H, s), 1.78 (3H, s).

b) Synthesis of (S)-N-acetyl-S-[1-(4-chlorobenzoyl)-5-methoxy-2-methyl-1H-indol-3-acetyl]cisteine 4-(bromobutyl) ester To a solution of (S)-N-acetyl-S-[1-(4-chlorobenzoyl)-5-methoxy-2-methyl-1H-indol-3-acetyl]cisteine (3.09 g, 6.14 mmoles) in N,N dimethylformamide (50 ml), sodium ethylate (0.42 g, 6.14 mmoles) and, after 30 minutes, 1,4-dibromobutane (2.18 ml, 18.00 mmoles) dissolved in 25 ml of N,N dimethylformamide, are added. The reaction mixture is left under stirring for 20 hours at room temperature, and then it is diluted with ethyl ether and washed with water. After the organic phase has been anhydrified with sodium sulphate, the solvent is removed by evaporation at reduced pressure. The obtained crude product is purified by chromatography on silica gel, eluting with cyclohexane/ethyl acetate 1/1. 1.7 g of the ester in the form of a yellow solid with m.p. 130°-134° C. are obtained.

c) Synthesis of (S)-N-acetyl-S-[1-(4-chlorobenzoyl)-5-methoxy-2-methyl-1H-indol-3-acetyl]cisteine 4-(nitroxy) butyl ester To a solution of the ester obtained at the end of the previous step (1.6 g, 2.5 mmoles) in acetonitrile. (30 ml) silver nitrate (0.6 g, 3.51 mmoles) is added. The reaction mixture is heated for 8 hours under reflux away from light. The formed salt is removed by filtration and the solution is evaporated at reduced pressure. The obtained residue is purified by chromatography on silica gel eluting with cyclohexane/ethyl acetate 4/6. 1.2 g of (S)-N-acetyl-S-[1-(4-chlorobenzoyl)-5-methoxy-2-methyl-1H-indol-3-acetyl] cisteine 4-(nitroxy)butyl ester in the form of an oil are obtained.

$^1$H-NMR (CDCl$_3$): 7.66 (2H, d), 7.48 (2H, d), 6.90 (2H, m), 6.68 (1H, m), 6.14 (1H, d), 4.77 (1H, m), 4.43 (2H, t), 4.08 (2H, m), 3.87 (2H, s), 3.83 (3H, s), 3.34 (2H, d), 2.38 (3H, s), 1.90 (3H, s), 1.78-1.70 (4H, m).

Elementary analysis:

| | | | | | |
|---|---|---|---|---|---|
| Calculated | C: 54.24% | H: 4.88% | N: 6.80% | S: 5.17% | Cl: 5.72% |
| Found | C: 54.32% | H: 4.93% | N: 6.91% | S: 5.13% | Cl: 5.84% |

EXAMPLE 4

Synthesis of (S)-N-acetyl-[2-fluoro-α-methyl-(1,1'-biphenyl)-4-acetyl]cisteine 4-(nitroxy)butyl ester (NCX 2131) having Formula

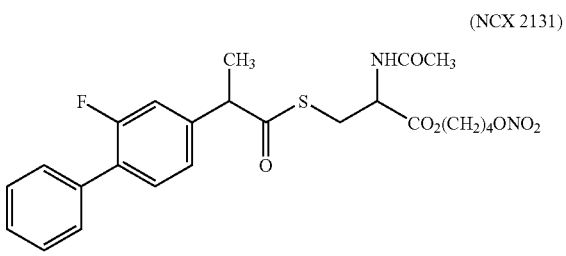
(NCX 2131)

The precursor is flurbiprofen (Formula IX), the precursor of B is N-acetylcisteine (formula CVIII)

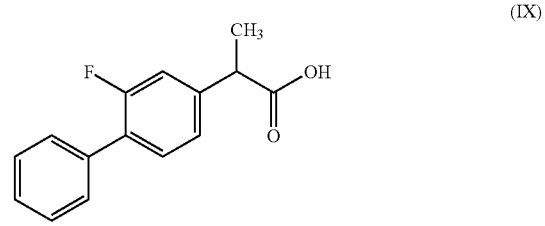
(IX)

(CVIII)

The NCX 2131 compound is synthetized according to the process described in Example 1. The substance appears as an oil. Yield: 26%

$^1$H-NMR (CDCl$_3$): 7.41-7.38 (6H, m), 7.10 (2H, m), 6.22 (1H, d), 4.78 (1H, m), 4.46 (2H, t), 4.13 (2H, t), 3.92 (1H, q), 3.36 (2H, d), 1.93 (3H, d), 1.76 (4H, d), 1.55 (3H, d).

Elementary analysis

| | | | | | |
|---|---|---|---|---|---|
| Calculated | C: 56.91% | H: 5.37% | N: 5.55% | S: 6.33% | F: 3.75% |
| Found | C: 56.99% | H: 5.41% | N: 5.66% | S: 6.41% | F: 3.83% |

EXAMPLE 5

Preparation of trans-3-[4-[α-methyl-[4-(–2-methyl-propyl)benzene]acetyloxy]-3-methoxyphenyl]-2-propenoyl 4-(nitroxy) butyl ester (NCX 2210) having Formula

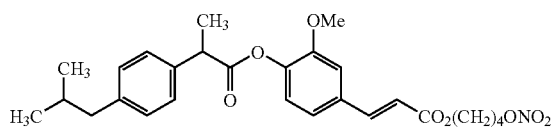
(NCX 2210)

The precursor is ibuprofen (Formula VII), the precursor of B is ferulic acid (formula DII):

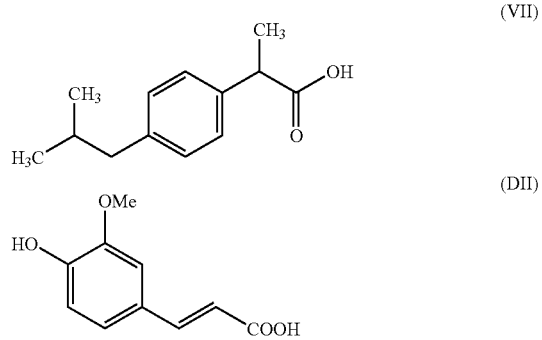
(VII)

(DII)

a) Synthesis of trans-3-[4-[α-methyl-[4-(–2-methylpropyl) benzene]acetyloxy]-3-methoxyphenyl]-2-propenoic acid To a solution of α-methyl-[4-(2-methylpropyl)benzene] acetic acid (5.03 g, 24.4 mmoles) in tetrahydrofuran (100 ml) and N,N-dimethylformamide (5 ml) 1,1-carbonyldiimidazole (4.25 g, 24.8 mmoles) is added. After 1 hour, the obtained solution is treated with ferulic acid (4.90 g, 25 mmoles), sodium ethylate (89 mg) is added and left at room temperature under stirring for 12 hours. The reaction mixture is washed with HCl 5%, then with water and lastly with brine. The organic phase is anhydrified with sodium sulphate and evaporated at reduced pressure.

The obtained residue is purified by chromatography on silica gel, eluting with ethyl acetate/n-hexane 7/3. 5.1 g of trans-3-[4-[α-methyl-[4-(–2-methylpropyl)benzene]acetyl]-3-methoxyphenyl]-2-propenoic acid as white solid, with m.p. 131°-137° C., are obtained.

$^1$H-NMR (CDCl$_3$): 7.72 (1H, d), 7.32 (2H, dd), 7.26 (1H, m), 7.16-7.07 (4H, m), 6.98 (1H, d), 6.37 (1H, d), 3.99 (1H, q), 3.73 (3H, s), 2.47 (2H, d), 1.88 (1H, m), 1.63 (3H, d), 0.92 (6H, d).

b) Synthesis of trans-3-[4-[α-methyl-[4-(–2-methylpropyl)benzene]acetyloxy]-3-methoxyphenyl]-2-propenoyl 4-bromobutyl Ester To a solution of trans-3-[4-[α-methyl-[4-(2-methylpropyl)-benzene]acetyloxy]-3-methoxyphenyl]-2-propenoic acid (5.33 g, 14 mmoles) in N,N-dimethylformamide (130 ml), sodium ethylate (1.2 g, 16 mmoles) is added under stirring. After 1 hour, to the obtained mixture 1,4-dibromobutane (10 g, 46 mmoles) is added and let react at room temperature for 12 hours. The reaction mixture is washed with HCl 5%, then with water and lastly with brine, the organic phase is anhydrified with sodium sulphate and evaporated at reduced pressure. The obtained residue is purified by chromatography on silica gel eluting with n-hexane/ethyl acetate 8/2. 4.46 g of trans-3-[4-hydroxy-[α-methyl-[4-(–2-methylpropyl)benzene]acetyl]-3-methoxyphenyl]-2-propenoyl 4-bromobutyl ester are obtained.

c) Synthesis of trans-3-[4-[α-methyl-[4-(–2-methylpropyl)benzene]acetyloxy]-3-methoxyphenyl]-2-propenoyl 4-(nitroxy) butyl Ester To a solution of trans-3-[4-[α-methyl-[4-(–2-methylpropyl)benzene]acetyloxy]-3-methoxyphenyl]-2-propenoyl 4-bromo-butyl ester (4 g, 7.72 mmoles) in acetonitrile (70 ml) silver nitrate (2.58 g, 15 mmoles) is added. The reaction mixture is heated under reflux for 2 hours away from light. At the end, the formed salt is removed by filtration and the solution is evaporated at reduced pressure. The recovered residue is purified by chromatography on silica gel, eluting with n-hexane/ethyl acetate 8/2. 2.4 g of trans-3-[4-[α-methyl-[4-(–2-methylpropyl)benzene]acetyloxy]-3-methoxyphenyl]-2-propenoyl 4-(nitroxy) butyl ester as an oil, are obtained.

$^1$H-NMR (CDCl$_3$): 7.62 (1H, d), 7.32 (2H, d), 7.15 (2H, d), 7.16-7.05 (2H, m), 6.96 (1H, d), 6.35 (1H, d), 4.51 (2H, t), 4.24 (2H, t), 3.99 (1H, q), 3.74 (3H, s), 2.48 (2H, d), 1.89-1.83 (5H, m), 1.62 (3H, d), 0.92 (6H, d).

Elementary analysis:

| | | | |
|---|---|---|---|
| Calculated | C: 64.91% | H: 6.66% | N: 2.82% |
| Found | C: 64.83% | H: 6.52% | N: 2.69% |

EXAMPLE 6

Synthesis of trans-3-[4-[2-fluoro-α-methyl-(1,1'-biphenyl)-4-acetyloxy]-3-methoxyphenyl]-2-propenoyl 4-(nitroxy) butyl ester (NCX 2216) having Formula

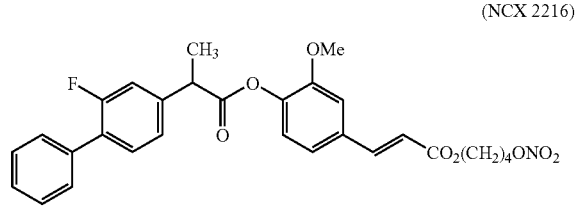
(NCX 2216)

The precursor is flurbiprofen (formula IX), the precursor of B is ferulic acid (formula DII)

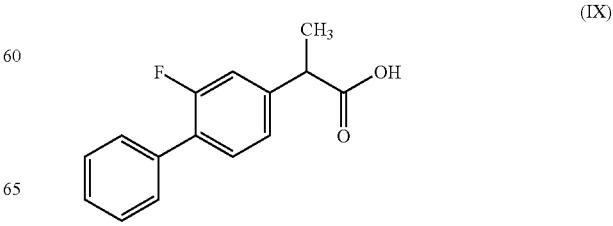
(IX)

-continued

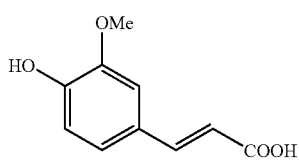
(DII)

The NCX 2216 compound is synthesized according to the process described in Example 5. The total process yield is 32%. The substance appears as an amorphous solid.

$^1$H-NMR (CDCl$_3$): 7.40-7.25 (9H, m), 7.07-7.01 (2H, d), 6.98 (1H, m), 6.38 (1H, d), 4.44 (2H, t), 4.46 (2H, t), 4.21 (2H, t), 4.04 (1H, q), 3.73 (3H, s), 1.72 (4H, m), 1.65 (3H, d).

Elementary analysis:

| Calculated | C: 64.79% | H: 5.25% | N: 2.62% | F: 3.53% |
|---|---|---|---|---|
| Found | C: 64.85% | H: 5.31% | N: 2.74% | F: 3.48% |

EXAMPLE 7

Preparation of N-(4-nitroxybutyryl)-β-alanyl-(L)-histidine-4-acetamido phenyl ester (NCX 2160) having Formula

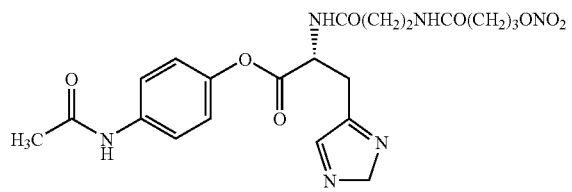
(NCX 2160)

wherein the precursor is acetaminofen (paracetamol) having formula (X) and the precursor of B is (L)-carnosine (NCX 2053) having formula (CI):

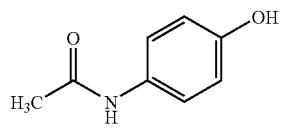
(X)

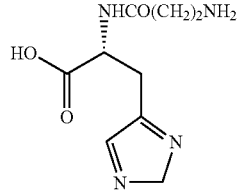
(CI)

a) Synthesis of N-(4-bromobutyryl)-β-alanyl-(L)-histidine

To a solution of carnosine (5 g, 22.1 mmoles) in N,N-dimethylformamide (80 ml), triethylamine (4.62 ml, 33.1 mmoles) and 4-bromobutyrylchloride (chloride of 4-bromobutyric acid-83.85 ml, 33.1 mmoles) are added. The solution is left under stirring for 24 hours at room temperature, then it is diluted with ethyl acetate and the organic phase is washed with water. The organic phase is then anhydrified with sodium sulphate and evaporated at reduced pressure. The obtained crude product is purified by chromatography on silica gel eluting with ethyl acetate, obtaining the final product.

b) Synthesis of N-(4-bromobutyryl)-β-alanyl-(L)-histidine-4-acetamidophenyl ester To a solution of N-(4-bromobutyryl)-β-alanyl-(L)-histidine (3 g, 8 mmoles) in chloroform (50 ml) and N,N-dimethylformamide (4 ml), paracetamol (1.21 g, 8 mmoles), N,N-dicyclohexyl carbodiimide (1.65-g, 8 mmoles) and dimethylaniinopyridine (0.04 g, 0.36 mmoles) are added under stirring. The mixture is let react at room temperature for 6 hours. Lastly, it is filtered, diluted with chloroform and washed with water. The organic phase is anhydrified with sodium sulphate and evaporated at reduced pressure. The obtained crude product is purified by chromatography on silica gel, eluting with ethyl acetate/n-hexane 7/3. N-(4-bromobutyryl)-β-alanyl (L)-histidine 4-acetamido phenyl ester is obtained.

c) Synthesis of N-(4-nitroxybutyryl)-β-alanyl-(L)-histidine-4-acetamidophenyl Ester To a solution of N-(4-bromobutyryl)-β-alanyl-(L)-histidine-4-acetamido phenyl ester (4 g, 7.87 mmoles) in acetonitrile (70 ml), silver nitrate (1.87 g, 11 mmoles) is added under stirring. The reaction mixture is heated for 5 hours under reflux, away from light. At the end, the formed salt is removed by filtration and the solution is evaporated at reduced pressure. The obtained residue is purified by chromatography on silica gel, eluting with n-hexane/ethyl acetate 3/7. The expected product is obtained with a yield of 17%.

Elementary analysis:

| Calculated | C: 51.39% | H: 5.34% | N: 17.19% |
|---|---|---|---|
| Found | C: 51.28% | H: 5.28% | N: 17.06% |

EXAMPLE 8

Preparation of N-acetyl-S-[(S)-α-(2-chlorophenyl)-6,7-dihydrothieno[3,2-c]pyridin-5 (4H)acetyl](S)-cisteine 4-(nitroxy) butyl ester (NCX 2136)

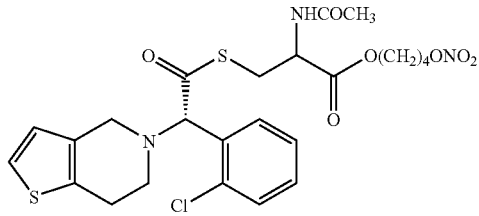
(NCX 2136)

wherein the precursor is clopidogrel having formula (XI) and the precursor of B is N-aceticisteine having formula (CVIII):

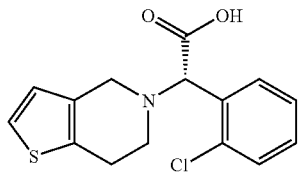
(XI)

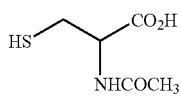
(CVIII)

The compound is synthetized following the procedure reported in Example 1. The yield is of 23%.

Elementary analysis:

| Calculated | C: 50.55% | H: 4.95% | N: 7.40% | S: 11.24% | Cl: 6.22% |
| Found | C: 50.70% | H: 4.99% | N: 7.60% | S: 11.20% | Cl: 6.15% |

EXAMPLE 9

Preparation of [3-methoxy-4-(4-nitroxybutyryloxy)phenyl]-2-trans-propenoyl-4-[(2-amino-3,5-dibromophenyl)methylamino]cyclohexanol Ester (NCX 2161)

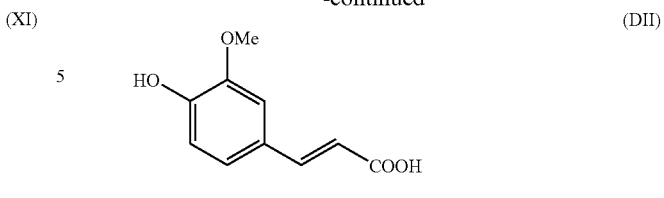
(DII)

a) Synthesis of 4-[(2-ter-butoxycarbonylamino-3,5-dibromophenyl)methylamino]trans cyclohexanol To a mixture of 4-[(2-amino-3,5-dibromophenyl)methylamino]cyclohexanol (5 g, 13.22 mmoles) in dioxane (35 ml) and water (50 ml), triethylamine (3.31 ml, 23.7 mmoles) and di-ter-butyldicarbonate (3.46 g, 15.86 mmoles) are added under stirring. After 24 hours, the solution is concentrated under vacuum, a HCl 1% solution until neutral pH (pH=7) is added and the organic phase is extracted with ethyl acetate. The organic phase is anhydrified with sodium sulphate and evaporated under vacuum. 4-[(2-ter-butoxycarbonylamino-3,5-dibromophenyl) methyl amino]cyclohexanol is obtained which is used without further purification.

b) Synthesis of (3-methoxy-4-hydroxyphenyl)-2-trans-propenoyl-4-[(2-ter-butoxycarbonylamino-3,5-dibromo phenyl)methylamino]cyclohexanol ester To a solution of ferulic acid (4 g, 20.5 mmoles) in tetrahydrofuran (40 ml) cooled at 0° C., 1,1'-carbonyldiimidazol (3.34 g, 20.5 mmoles) is added. After 10 minutes, the solution is treated with 4-[(2-ter-butoxycarbonylamino-3,5-dibromophenyl) methyl amino]cyclohexanol (9.8 g, 20.5 mmoles) and let react at room temperature for 4 hours. The reaction mixture is concentrated under vacuum, treated with methylen chloride, washed with a HCl 1% solution and then

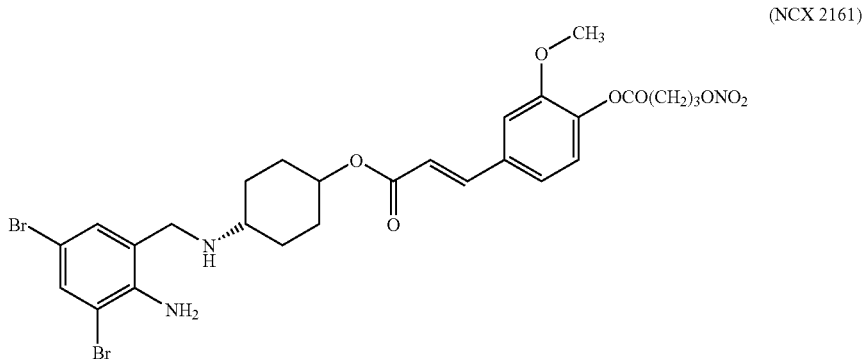
(NCX 2161)

wherein the precursor is ambroxol having formula (XII) and the precursor of B is represented by ferulic acid having formula (DII):

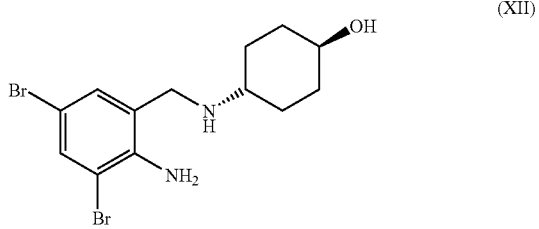
(XII)

with water. The organic phase is anhydrified with sodium sulphate and then evaporated under vacuum. The obtained residue is purified by chromatography on silica gel, eluting with n-hexane/ethyl acetate 1/1. (3-methoxy-4-hydroxyphenyl)-2-trans propenoyl 4-[(2-ter-butoxycarbonylamino-3,5-dibromo phenyl) methylamino]cyclohexanol ester, is obtained.

c) Synthesis of [3-methoxy-4-(4-bromobutyryl-oxy)phenyl]-2-trans propenoyl-4-[(2-ter-butoxycarbonylamino-3,5-dibromo-phenyl) methylamino]cyclohexanol ester To a solution of (3-methoxy-4-hydroxyphenyl)-2-trans propenoyl-4-(2-ter-butoxycarbonylamino-3,5-dibromo-phenyl) methylamino]cyclohexanol ester (4 g, 6.11 mmoles) in tetrahydrofuran (80 ml), triethylamine (0.85 ml, 6.11 mmoles) and 4-bromobutyrylchloride (0.7 ml, 6.1 mmoles)

are added under stirring. It is let react at room temperature for 8 hours and then the organic solvent is evaporated at reduced pressure. The obtained crude product is treated with ethyl acetate and the organic phase washed with water. The organic phase is anhydrified with sodium sulphate and evaporated under vacuum. The residue is purified by chromatography on silica gel eluting with n-hexane/ethyl acetate 7/3. [3-methoxy-4-(4-bromobutyryloxy)-phenyl]-2-trans propenoyl 4-[(2-ter-butoxycarbonylamino-3,5-dibromo phenyl) methylamino]cyclohexanol ester is obtained.

d) Synthesis of [3-methoxy-4-(4-nitroxybutyryloxy)phenyl]-2-trans-propenoyl 4-[(2-ter-butoxycarbonylamino-3,5-dibromo phenyl) methylamino]cyclohexanol Ester To a solution of [3-methoxy-4-(4-bromobutyryloxy)phenyl]-2-trans-propenoyl-4-[(2-ter-butoxy carbonylamino-3,5-dibromophenyl)methylamino]cyclohexanol ester (4 g, 4.98 mmoles) in acetonitrile (70 ml), silver nitrate (0.87 g, 4.98 mmoles) is added under stirring. It is heated under reflux for 7 hours away from light and lastly the formed salt is removed by filtration. The organic solution is evaporated at reduced pressure. The obtained residue is purified by chromatography on silica gel cluting with n-hexane/ethyl acetate 7/3. [3-methoxy-4-(4-nitroxybutyryloxy)phenyl]-2-tranipropenoyl 4-[(2-ter-butoxycarbonylamino-3,5-dibromo-phenyl)methylamino]cyclohexanol ester is obtained.

e) Synthesis of [3-methoxy-4-(4-nitroxybutyryloxy)phenyl]-2-transpropenoyl 4-[(2-amino-3,5-dibromo phenyl) methylamino]cyclohexanol ester To a solution of (3-methoxy-4-(4-nitroxybutyryloxy)phenyl]-2-transpropenoyl 4-[(2-ter-butoxycarbonylamino-3,5-dibromo phenyl)-methylamino]cyclohexanol ester (2 g, 2.54 mmoles) in ethyl acetate (50 ml), cooled at 0° C. and maintained under stirring, a HCl 5N solution in ethyl acetate (3.17 ml) is added. The solution is left under stirring at 0° C. for 4 hours. Lastly, the precipitate is filtered. The obtained crude product is treated with ethyl acetate, to which a 5% sodium bicarbonate solution is added. It is shaken and the bicarbonate solution is substituted with an equal part of water. It is shaken again, the organic phase is recovered, anhydrified with sodium sulphate and evaporated at reduced pressure. [3-methoxy-4-(4-nitroxybutyryloxy)phenyl]2-2-transpropenoyl-4-[(2-amino-3,5-dibromophenyl) methylamino]cyclohexanol ester is obtained.

Yield: 36%

Elementary analysis:

| Calculated | C: 47.30% | H: 4.56% | N: 6.15% | Br: 23.31% |
| Found | C: 47.26% | H: 4.53% | N: 6.00% | Br: 23.42% |

EXAMPLE 10

Preparation of [4-amino-[[3-methoxy-4-(4-nitroxybutyryloxy)phenyl]-2-trans propenoyl]-1-hydroxy-butyliden]-bisphosphonic Acid (NCX 2211),

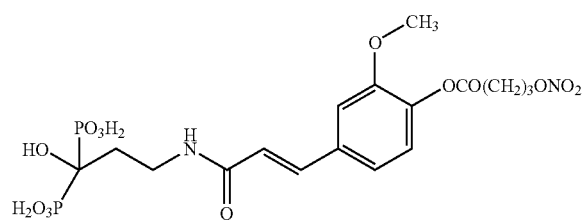

(NCX 2211)

wherein the precursor is alendronic acid of formula (XIII) and the precursor of B is the ferulic acid (formula DII):

(XIII)

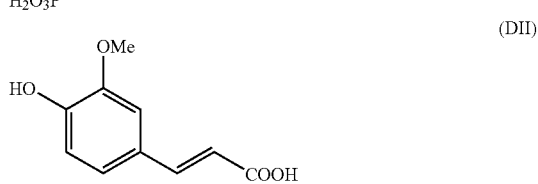

(DII)

a) Synthesis of [3-methoxy-4-(4-bromobutyryloxy)phenyl]-2-trans-propenoic Acid

To a solution of ferulic acid (1.2 g, 6.11 mmoles) in tetrahydrofuran (80 ml), triethylamine (0.85 ml, 6.11 mmoles) and 4-bromobutyrylchloride (0.7 ml, 6.11 mmoles) are added under stirring. It is let react at room temperature for 3 hours and then evaporated at reduced pressure. The obtained crude product is treated with ethyl acetate and the organic phase washed with water. The organic phase is then anhydrified with sodium sulphate and evaporated under vacuum. The obtained residue is purified by chromatography on silica gel eluting with chloroform/methanol 8/2. The [3-methoxy-4-(4-bromobutyryloxy)-phenyl]-2-trans propenoic acid is lastly isolated.

b) Synthesis of the (3-methoxy-4-(4-nitroxybutyryloxy) phenyl]-2-trans Propenoic Acid To a solution of [3-methoxy-4-(4-bromobutyryloxy)phenyl]-2-trans-propenoic acid (1.5 g, 4.5 mmoles) in acetonitrile (70 ml) silver nitrate (0.87 g, 4.98 mmoles) is added under stirring. The mixture is heated under reflux and, under stirring, it is reacted for 3 hours sheltered from the light. The formed salt is removed by filtration and the organic phase is evaporated at reduced pressure. The obtained residue is purified by chromatography on silica gel column, eluting with chloroform/methanol 8/2. The [3-methoxy-4-(4-nitroxybutyroyloxy) phenyl]-2-trans propenoic acid is recovered.

c) Synthesis of [4-amino-[(3-methoxy-4-(4-nitroxybutyryloxy)phenyl]-2-trans propenoyl)-1-hydroxy-butyliden] bisphosphonic Acid To a solution of [3-methoxy-4-(4-nitroxybutyroyloxy)-phenyl]-2-trans propenoic acid (2 g, 6.4 mmoles) in N,N-dimethylformamide (30 ml), cooled at 0° C., N,N'dicyclohexylcarbodiimide (1.3 g, 6.4 mmoles) and 1-hydroxybenzotriazol (1.04 g, 7.68 mmoles) are added under stirring. After 30 minutes alendronic acid (1.6 g, 6.4 mmoles) is added. The reaction mixture is left under stirring at room temperature for 7 hours. At the end, it is acidified with a HCl 5% solution and the organic phase is extracted with ethyl acetate. The organic phase is washed with brine, anhydrified with sodium sulphate and evaporated at reduced pressure. The crude product is purified by chromatography on silica gel column eluting with methylene chloride/methanol 8/2, obtaining the [4-amino-[(3-methoxy-4-(4-nitroxybutyroyloxy) phenyl]-2-trans propenoyl]-1-hydroxy butyliden]bisphosphonic acid. Yield: 11%.

Elementary analysis:

| Calculated | C: 19.71% | H: 4.36% | N: 5.07% | P: 11.17% |
| Found | C: 19.56% | H: 4.28% | N: 5.04% | P: 11.25% |

EXAMPLE 11

Preparation of S-[[2-[4-(4-chlorophenyl)phenylmethyl)-1-piperazinyl]ethoxy]acetyl]penicillamine 4-(nitroxy)butyl ester (NCX 2060) having Formula -continued

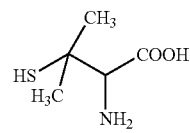
(CV)

a) Synthesis of S-[[2-[4-[(4-chlorophenyl)phenylmethyl]-1-piperazinyl]ethoxy]acetyl]N-ter-butoxycarbonylpenicillamine-4-(nitroxy)butyl Ester The compound is prepared according to the procedure reported in Example 1, by using N-ter-butoxycarbonyl-penicillamine instead of N-acetyl cisteine.

b) Synthesis of S-[[2-[4-[(4-chlorophenyl)phenylmethyl]-1-piperazinyl]ethoxy]acetyl]-penicillamine-4-(nitroxy)butyl Ester.

The compound is obtained from the previous one by following the procedure described in step e) of Example 9 to remove the protective group N-ter-butoxycarbonyl and recover the aminic function. Yield: 26%.

Elementary analysis:

| Calculated | C: 55.78% | H: 6.49% | N: 8.43% | S: 4.80% | Cl: 5.31% |
| Found | C: 55.61% | H: 6.31% | N: 8.29% | S: 4.93% | Cl: 5.43% |

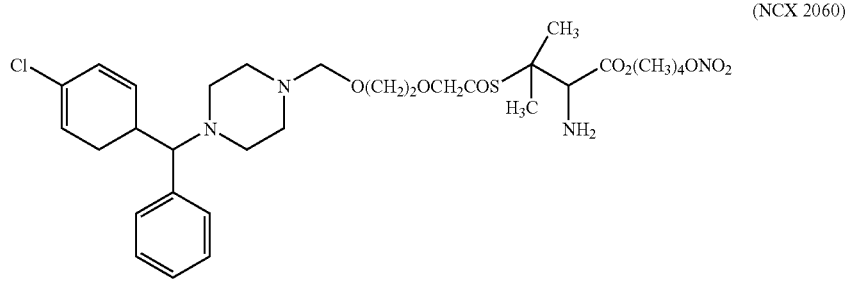
(NCX 2060)

wherein the precursor is cetirizine of formula (XIV) and the precursor of B is penicillamine (formula CV):

EXAMPLE 12

Preparation of N-acetyl-S-[(S)-1-[N-[1-(ethoxycarbonyl)-3-phenylpropyl]-L-alanyl]-L-prolin]cisteine 4-(nitroxy)butyl ester of formula (NCX 2134)

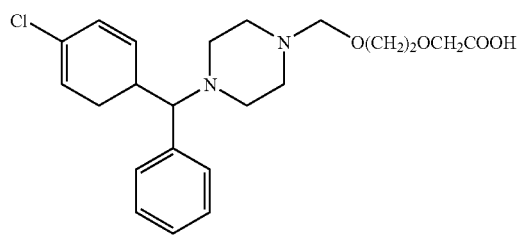
(XIV)

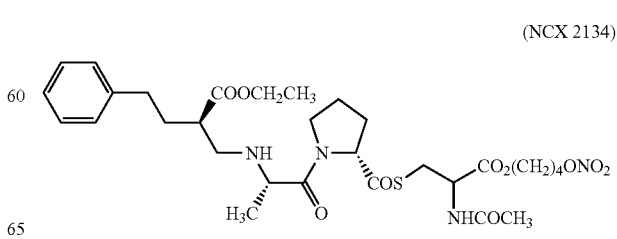
(NCX 2134)

wherein the precursor is enalapril of formula (XV) ard the precursor of B is N-acetylcisteine (formula CVIII):

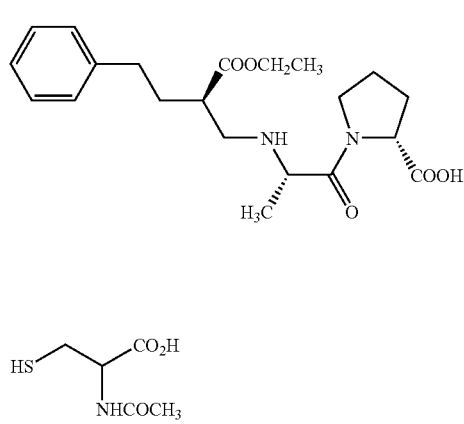

(XV)

(CVIII)

The compound is synthetized following the procedure reported in Example 1. Yield: 27%

Elementary analysis

| | | | | |
|---|---|---|---|---|
| Calculated | C: 55.18% | H: 6.79% | N: 8.62% | S: 4.91% |
| Found | C: 55.30% | H: 6.85% | N: 8.71% | S: 4.85% |

EXAMPLE 13

Preparation of 3-[4-D-α-aminobenzylpenicillaminoyloxy]-3-methoxyphenyl]-2-trans propenoyl 4-(nitroxy)butyl ester (NCX 2080) having Formula

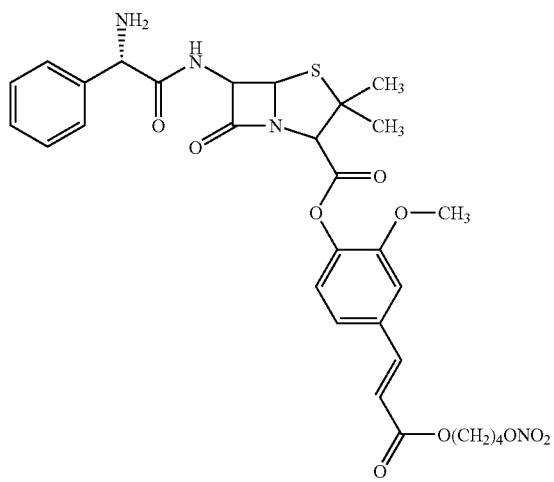

(NCX 2080)

wherein the precursor is represented by ampicilline (formula XVI) and the precursor of B is ferulic acid (formula DII):

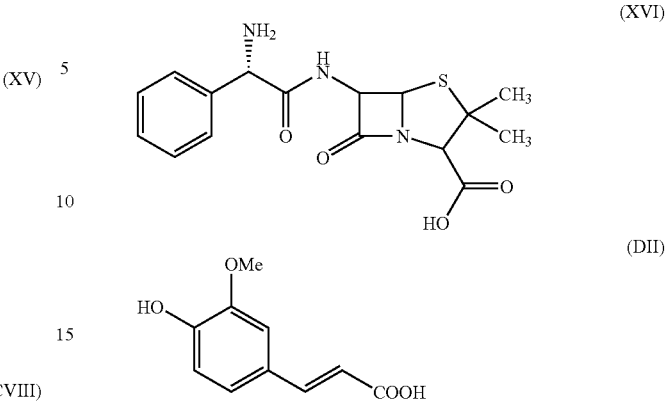

(XVI)

(DII)

The compound is synthetized following the method reported in Example 5. Yields: 11%.

Elementary analysis

| | | | | |
|---|---|---|---|---|
| Calculated | C: 56.04% | H: 5.33% | N: 8.75% | S: 4.99% |
| Found | C: 56.15% | H: 5.48% | N: 8.65% | S: 4.83% |

EXAMPLE 14

Preparation of 9-[[2-[-N-acetyl-S-(4-nitroxybutyroyl)cisteinyl]ethoxy]-methyl]guanine of formula (NCX 2135)

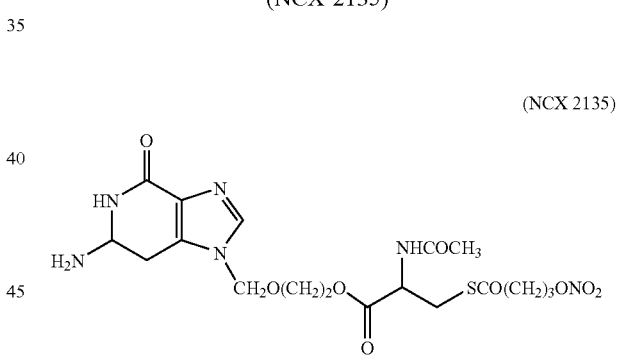

(NCX 2135)

wherein the precursor is acyclovir of formula (XVII) and the precursor of B is N-acetylcisteine (formula CVIII):

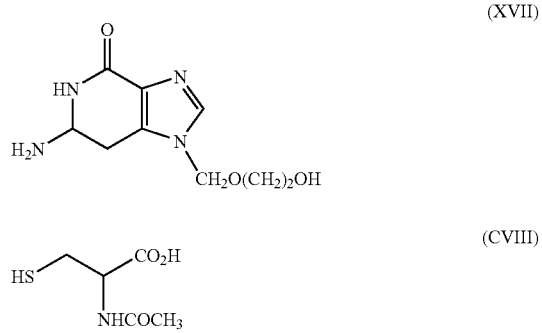

(XVII)

(CVIII)

a) Synthesis of N-acetyl-S-(4-bromobutyroyl)cisteine

A solution containing 4-bromobutyric acid (5.1 g, 30.6 mmoles) and 1,1'-carbonyldiimidazole (5.61 g, 34.6 mmoles) in chloroform (50 ml) is prepared and it is left under stirring at room temperature for 1 hour. To the reaction mixture a solution of N-acetylcisteine (5 g, 30.6 mmoles) in N,N-dimethylformamide (5 ml) containing sodium ethylate (50 mg) is added. It is let react under stirring and after 24 hours the solution is washed with HCl 1% and then with brine. The organic phase is anhydrified with sodium sulphate and evaporated at reduced pressure. The obtained crude product is purified by chromatography on silica gel column, eluant ethyl acetate/chloroform 7/3, lastly obtaining N-acetyl-S-(4-bromobutyroyl) cisteine.

b) Synthesis of N-acetyl-S-(4-nitroxybutyroyl)cisteine

To a solution of N-acetyl-S-(4-bromobutyroyl)cisteine (3 g, 9.6 mmoles) in acetonitrile (70 ml) silver nitrate (1.7 g, 10 mmoles) is added. The reaction mixture is heated under stirring under reflux for 2 hours away from light. The formed salt is removed by filtration and the solution is evaporated at reduced pressure. The obtained residue is purified by chromatography on silica gel column eluting with ethyl acetate/chloroform 7/3, lastly obtaining N-acetyl-S-(4-nitroxybutyroyl)cisteine.

c) Synthesis of 9-[[2-[N-Acetyl-S-(4-nitroxybutyroyl) cisteinyl]ethoxy]methyl]guanine A solution of N-acetyl-S-(4-nitroxybutyroyl)cisteine (2.8 g, 9.6 mmoles) and 1,1'-carbonyldiimidazole (1.55 g, 9.6 mmoles) in tetrahydrofuran (50 ml) is prepared and left under stirring at room temperature for 1 hour. The reaction mixture is treated with acyclovir (2.16 g, 9.6 mmoles). After 6 hours of reaction at room temperature, the solution is evaporated at reduced pressure, the obtained residue treated with ethyl acetate and washed with brine. The organic phase is anhydrified with sodium sulphate and then dried under vacuum. The obtained residue is purified by chromatography on silica gel column eluting with ethyl acetate. 9-[[2-[N-acetyl-S-(4-nitroxybutyroyl)cisteinyl-]ethoxy]methyl] guanine is obtained. Yields: 9%.

Elementary analysis

| Calculated | C: 35.25% | H: 3.95% | N: 13.76% | S: 47.05% |
| Found | C: 35.38% | H: 3.99% | N: 13.84% | S: 47.20% |

EXAMPLE 15

Preparation of trans-3-[4-(5-amino-2-hydroxybenzoyl)-3-methoxyphenyl]2-propenoyl 4-(nitroxy) butyl Ester (NCX 2212),

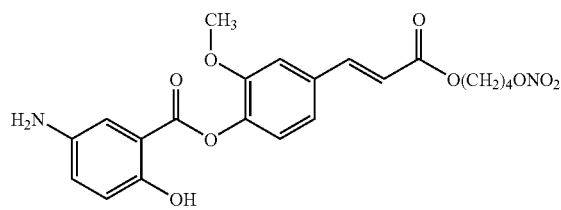

(NCX 2212)

wherein the precursor is mesalamine of formula (XVIII) and the precursor of B is the ferulic acid (formula DII):

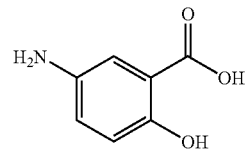

(XVIII)

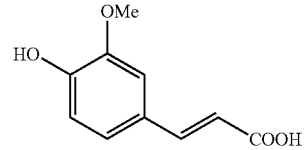

(DII)

a) synthesis of trans-3-[4-(5-ter-butyloxycarbonylamino-2-hydroxybenzoyl)-3-methoxyphenyl]2-propenoic acid 4-(nitroxy)butyl Ester The compound is synthetized according to the procedure reported in Example 5, first protecting the primary aminic group of the mesalamine as described in Example 9, step a).

b) Obtaining of trans-3-[4-(5-amino-2-hydroxybenzoyl)-3-methoxyphenyl]2-propenoyl 4-(nitroxy)butyl Ester The final compound is obtained by hydrolizing the bond between the aminic function and the N-ter-butoxycarbonyl protective group as described in Example 9, step e). Yields: 28%.

Elementary analysis:

| Calculated | C: 56.49% | H: 4.96% | N: 6.30% |
| Found | C: 56.55% | H: 4.82% | N: 6.45% |

EXAMPLE 16

Preparation of 6-methylen-5-hydroxy-10[2-hydroxy-5-(4-nitroxybutyryloxy) benzoyl]tetracycline of Formula (NCX 2163)

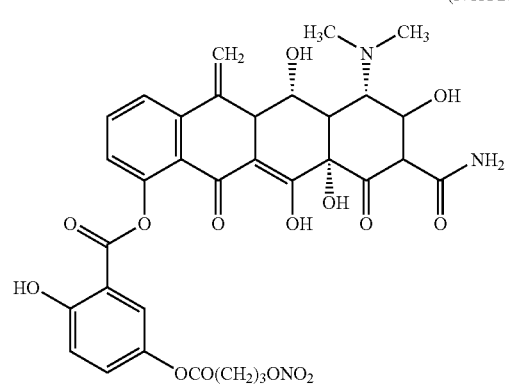

(NCX 2136)

wherein the precursor is methacycline of formula (XIX) and the precursor of B is the gentisic acid (formula DIII):

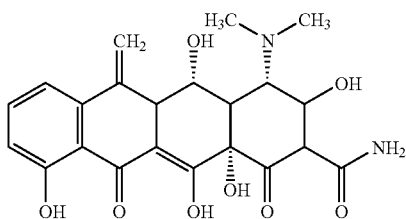

(XIX)

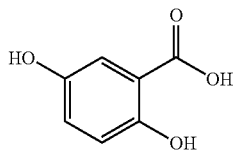

(DIII)

a) Synthesis of the 5-(4-bromobutyryloxy)-2-hydroxybenzoic Acid

In a solution of 4-bromobutyrylchloride (3 g, 16.17 mmoles) in tetrahydrofuran (50 ml), cooled at 0° C., triethylamine (4.5 ml, 32.34 mmoles) and then gentisic acid (2.4 g, 16.16 mmol) are dropped under stirring. It is allowed to react at 0° C. for 4 hours, under stirring, then it is evaporated at reduced pressure. The obtained crude product is treated with ethyl acetate, the organic phase is washed with HCl 1% and then brine. The organic phase is anhydrified with sodium sulphate and dried. The obtained residue is purified by chromatography on silica gel column, eluting with methylene chloride/methanol 95/5, obtaining the 5-(4-bromobutyryloxy)-2-hydroxy-benzoic acid.

b) Synthesis of 5-(4-nitroxybutyroyloxy)-2-hydroxybenzoic Acid

To a solution of 5-(4-bromobutyryloxy)-2-hydroxy-benzoic acid (3 g, 9.6 mmoles) in acetonitrile (150 ml) silver nitrate (1.7 g, 10 mmoles) is added under stirring. The mixture is heated under reflux for 7 hours away from light. Lastly, the formed salt is removed by filtration and the solution is evaporated at reduced pressure. The obtained residue is purified by chromatography on silica gel column, eluting with methylene chloride/methanol 95/5. In this way, the 5-(4-nitroxybutyryloxy)-2-hydroxy-benzoic acid is isolated at the pure state.

c) Synthesis of 6-methylen-5-hydroxy-10µ-hydroxy-5-(4-nitroxybutyryloxy) benzoyl)tetracycline A solution of 5-(4-nitroxybutyryloxy)-2-hydroxy-benzoic acid (5 g, 16.4 mmoles) and 1,1'-carbonyldiimidazole (2.67 g, 16.4 mmoles) in tetrahydrofuran (70 ml) is maintained under stirring at room temperature for 1 hour. Adriamycin (7.2 g, 16.4 mmoles) is added. It is reacted under stirring for 12 hours at room temperature. The organic solution is then evaporated at reduced pressure, and the obtained residue is treated with ethyl acetate and washed with brine. The organic phase, anhydrified with sodium sulphate, is dried under vacuum. The obtained residue is purified by chromatography on silica gel column eluting with ethyl acetate. 6-methylen-5-hydroxy-10[2-hydroxy-5-(4-nitroxybutyryloxy)benzoyl]tetracycline is obtained. Yield: 19%.

Elementary analysis:

| Calculated | C: 55.84% | H: 4.40% | N: 5.95% |
| Found | C: 55.95% | H: 4.55% | N: 5.98% |

EXAMPLE 17

Preparation of 5-[[3-[3-methoxy-4-(4-nitroxy)butyryloxy]phenyl-2-transpropenoyl]amino)-1,2,3,4-tetrahydroacridine (NCX 2214)

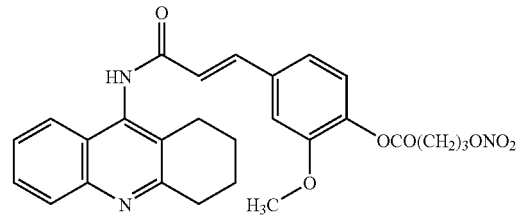

(NCX 2214)

wherein the precursor is tacrine of formula (XX) and the precursor of B is the ferulic acid (formula DII):

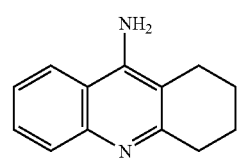

(XX)

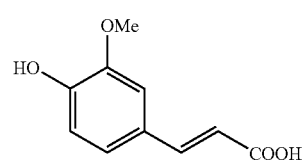

(DII)

The compound is synthetized according to the procedure reported in Example 10. Yield 7%

Elementary analysis

| | | | |
|---|---|---|---|
| Calculated | C: 64.13% | H: 5.38% | N: 8.34% |
| Found | C: 64.28% | H: 5.46% | N: 8.47% |

EXAMPLE 18

Preparation of [1S-[1α,3′,7β,8β,(2S*,4S*)]]-2,2-dimethylbutanoic acid 1,2,3,7,8,8-hexahydro-3,7-dimethyl-8-[tetrahydro-4-[2-hydroxy-5-(4-nitroxy-butyryloxy) benzoyl-oxy[-6-oxo-2H-piran-2-yl] ethyl]-1-naphthalenyl ester (NCX 2164)

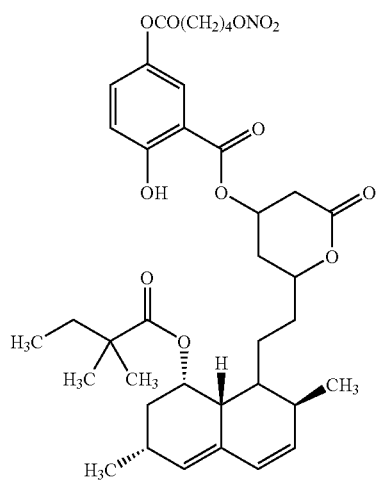

(NCX 2164)

wherein the precursor is simvastatine of formula (XXI) and the precursor of B is the gentisic acid (formula DIII):

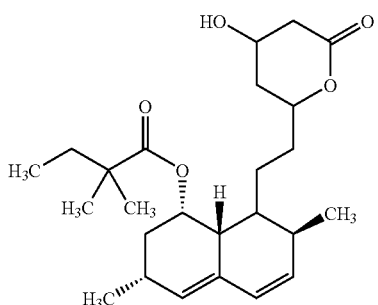

(XXI)

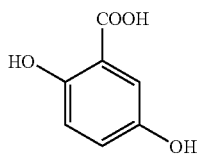

(DIII)

The compound is synthetized following the method described in Example 16. Yield: 13%.

Elementary analysis:

| | | | |
|---|---|---|---|
| Calculated | C: 63.50% | H: 7.06% | N: 2.01% |
| Found | C: 63.68% | H: 7.21% | N: 2.19% |

EXAMPLE 19

Preparation of 5-methoxy-2-[[[4-[N-[4-(nitroxy)butyl-β-alanyl](L)-histidinyloxy]-3,5-dimethyl-2-pyridinyl]methyl]sulphinyl]-1H-benzimidazole (NCX 2062)

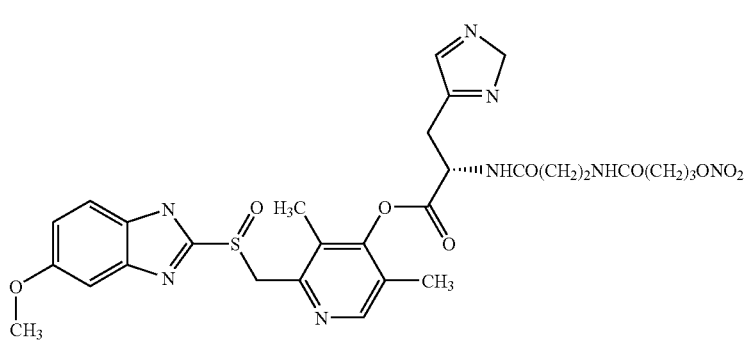

(NCX 2062)

wherein the precursor is 4-hydroxyomeprazol of formula (XXII), obtained by treating omeprazol as described in Acta Chem. Scand. 43, 6 1989 pages 549-568 and the precursor of B is carnosine (formula CI):

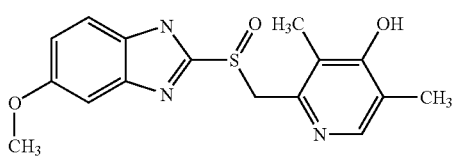
(XXII)

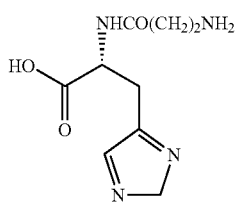
(CI)

The compound is synthetized according to the process described in Example 7. Yield: 25%

Elementary analysis:

| | | | | |
|---|---|---|---|---|
| Calculated | C: 51.97% | H: 4.96% | N: 16.79% | S: 4.78% |
| Found | C: 51.81% | H: 4.80% | N: 16.68% | S: 4.92% |

EXAMPLE 20

Preparation of N-nicotinoyl-O-alanyl (L)-histidine 4-(nitroxy)butyl ester (NCX 2073)

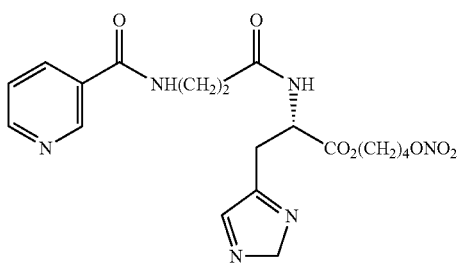
(NCX 2073)

wherein the precursor is nicotinamide of formula (XXIII) and the precursor of B is carnosine (formula CI):

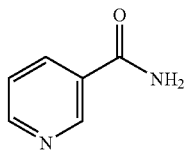
(XXIII)

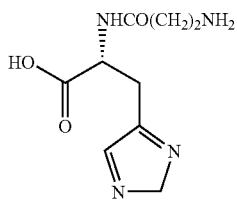
(CI)

a) Synthesis of N-nicotinoyl-β-alanyl (L)-histidine

To a solution of nicotinic acid (2.5 g, 20.5 mmoles) in tetrahydrofuran (40 ml) cooled at 0° C., 1,1'-carbonyldiimidazol (3.34 g, 20.5 mmoles) is added under stirring. After 10 minutes to the solution (L)-carnosine (4.6 g, 20.5 mmoles) is added and it is left under stirring at room temperature for 4 hours. The reaction mixture is concentrated under vacuum, treated with methylene chloride, washed with HCl 1% and then with water. The organic phase is anhydrified with sodium sulphate and evaporated under vacuum. The obtained residue is chromatographed on silica gel column, eluting with ethyl acetate. N-nicotinoyl-β-alanyl (L)-histidine is recovered.

b) Synthesis of N-nicotinoyl-β-alanyl (L)-histidine 4-bromobutyl Ester

To a solution of N-nicotinoyl-β-alanyl-(L)-histidine (9.9 g, 30.1 mmoles) in tetrahydrofuran (200 ml) triphenylphosphine (23.7 g, 90.3 mmoles) and carbon tetrabromide (28.85 g, 90.3 mmoles) are added under stirring. The reaction mixture is left under stirring at room temperature for 24 hours. Lastly, the solvent is removed by evaporation at reduced pressure. The obtained crude product is purified by chromatography on silica gel column eluting with n-hexane/ethyl acetate 1/1. N-nicotinoyl-β-alanyl-(L)-histidine 4-bromobutyl ester is obtained.

c) Synthesis of N-nicotinoyl-β-alanyl (L)-histidine 4-nitroxybutyl Ester

To a solution of N-nicotinoyl-β-alanyl (L)-histidine 4-bromobutyl ester (0.91 g, 1.96 mmoles) in acetonitrile (20 ml) silver nitrate (0.66 g, 3.92 mmoles) is added under stirring. The reaction mixture is heated to reflux under stirring for 4 hours away from light. Lastly, the formed salt is removed by filtration and the solution is evaporated at reduced pressure. The obtained residue is purified by chromatography on silica gel column eluting with n-hexane/ethyl acetate 1/1. N-nicotinoyl-β-alanyl-(L)-histidine 4-nitroxybutyl ester is obtained. Yields: 32%.

Elementary analysis:

| Calculated | C: 49.50% | H: 5.54% | N: 19.32% |
|---|---|---|---|
| Found | C: 49.35% | H: 5.28% | N: 19.17% |

EXAMPLE 21

Preparation of N-acetyl-S-(4-nitroxybutyroyl) cisteine 1-[(1-methylethyl) amino]-3-(1-naphthalenoxy)-2-propanol Ester (NCX 2132)

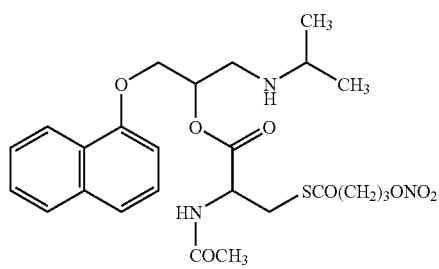
(NCX 2132)

wherein the precursor is propranolol of formula (XXIV) and the precursor of B is N-acetylcisteine (formula CVIII):

(XXIV)

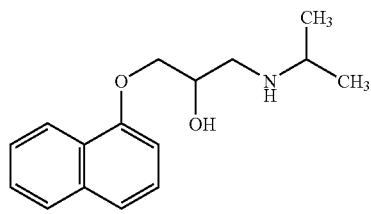

(CVIII)

The compound is synthetized with the process described in Example 14. Yields: 7%.

Elementary analysis:

| Calculated | C: 56.04% | H: 6.21% | N: 7.88% | S: 5.98% |
|---|---|---|---|---|
| Found | C: 56.13% | H: 6.35% | N: 7.91% | S: 6.04% |

EXAMPLE 22

Preparation of 2-(ter-butylamino)-1-[4-hydroxy-3-[N-acetyl-S-(4-nitroxybutyryl)-penicillaminoyl]oxyphenyl]ethanol (NCX 2133)

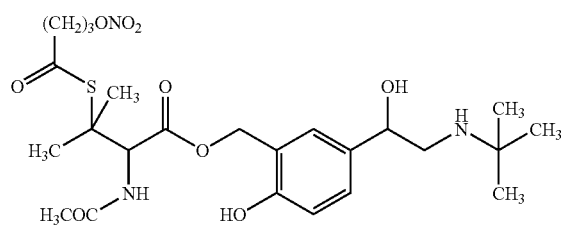
(NCX 2133)

wherein the precursor is salbutamol (albuterol) of formula (XXV) and the precursor of B is N-acetylpenicillamine (formula CV):

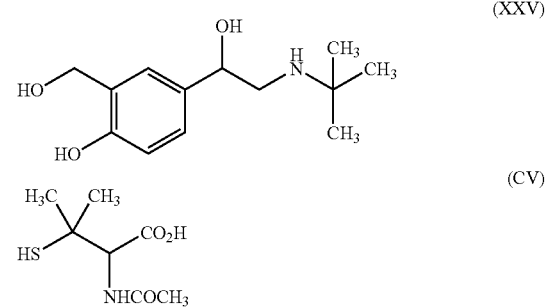
(XXV)

(CV)

The compound is synthetized by following the procedure reported in Example 14, using N-acetyl penicillamine instead of N-acetylcisteine. Yields: 43%

Elementary analysis:

| Calculated | C: 53.01% | H: 6.86% | N: 7.76% | S: 5.89% |
|---|---|---|---|---|
| Found | C: 53.19% | H: 6.80% | N: 7.66% | S: 5.72% |

EXAMPLE 23

Preparation of 7-[2-hydroxy-3-[3-methoxy-5-(4-nitrooxybutyryloxybenzoyl]trans-2-propenoyl]theophylline (NCX 2213)

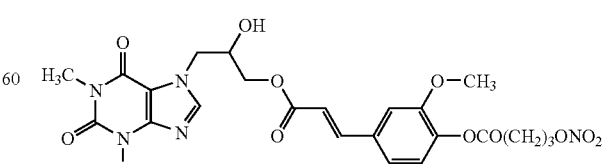
(NCX 2213)

wherein the precursor is the diphylline of formula (XXVI) and the precursor of B is the ferulic acid (formula DII):

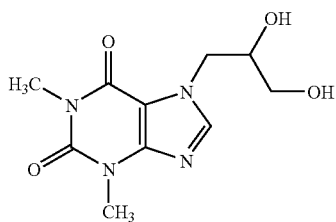
(XXVI)

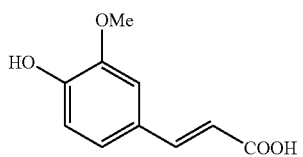
(DII)

The drug is synthesized according to the process described in Example 9. Yield: 22%

Elementary analysis:

| Calculated | C: 51.31% | H: 4.84% | N: 12.52% |
|---|---|---|---|
| Found | C: 51.50% | H: 4.91% | N: 12.68% |

EXAMPLE 24

Preparation of N-acetyl-S-(2-acetylbenzoyl)cisteine 4-(nitroxy)butyl Ester (NCX 2138) of Formula

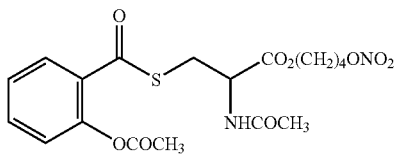
(NCX 2138)

wherein the precursor is acetylsalicylic acid of formula (XXVII) and the precursor of B is N-acetylcisteine (formula CVIII):

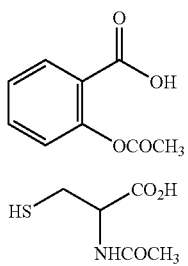
(XXVII)

(CVIII)

The compound is synthetized according to the process described in Example 1. Yield 36%.

Elementary analysis

| Calculated | C: 48.85% | H: 5.01% | N: 6.36% | S: 7.24% |
|---|---|---|---|---|
| Found | C: 48.75% | H: 5.02% | N: 6.28% | S: 7.12% |

EXAMPLE 25

Preparation of 4-[3-[3-methoxy-5-(4-nitroxybutyryloxy)phenyl]-2-propenoyloxy]-2-methyl-N-2-pyridinyl-2H-1,2-benzothiazin-3-carboxamide-1,1-dioxide (NCX2215)

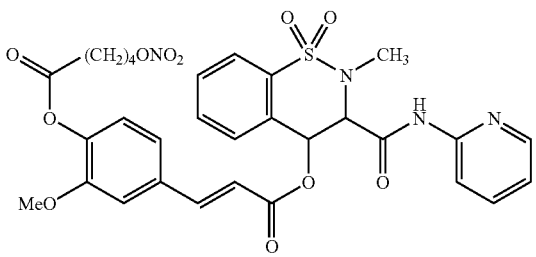
(NCX 2215)

wherein the precursor is piroxicam of formula (XXVIII) and the precursor of B is ferulic acid (formula DII):

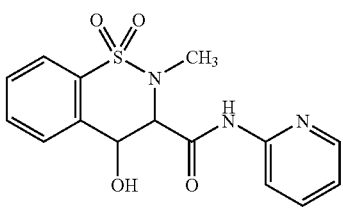
(XXVIII)

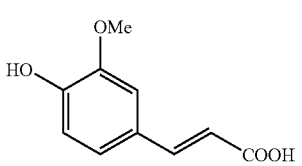
(DII)

The compound is synthetized according to the process reported in Example 9. Yield 18%.

Elementary analysis

| Calculated | C: 55.11% | H: 4.47% | N: 8.60% | S: 4.90% |
|---|---|---|---|---|
| Found | C: 55.18% | H: 4.52% | N: 8.71% | S: 4.98% |

EXAMPLE 26

Preparation of S-[2-[(2,6-dichlorophenyl)amino)benzeneacetiloxy]penicillamine 4 (nitroxy)butyl Ester (NCX 2061) of Formula

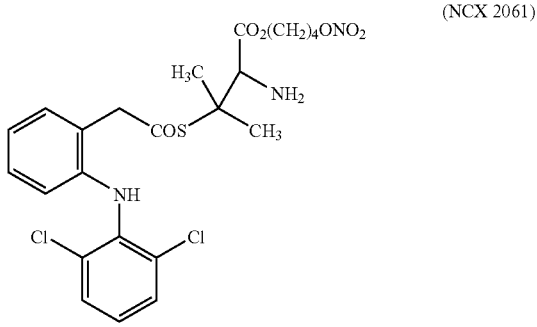

(NCX 2061)

wherein the precursor is diclofenac of formula (XXIX) and the precursor of B is penicillamine (formula CV):

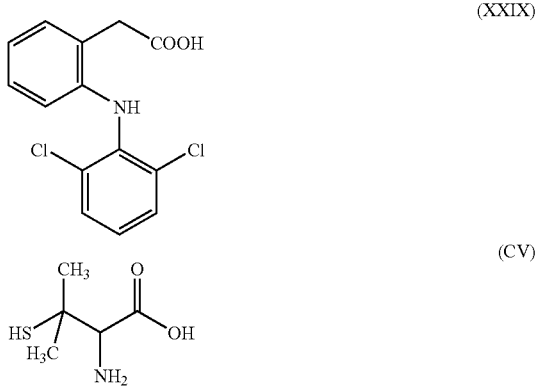

The compound is synthetized according to the process described in Example 11. Yield 21%.

Elementary analysis

| | | | | | |
|---|---|---|---|---|---|
| Calculated | C: 50.72% | H: 5.00% | N: 7.75% | S: 5.89% | Cl: 13.02% |
| Found | C: 50.61% | H: 4.89% | N: 7.81% | S: 6.01% | Cl: 13.21% |

Pharmacological Tests

EXAMPLE

Acute Toxicity

Acute toxicity has been evaluated by administering to a group of 10 rats weighing 20 g a single dose of each of the tested compounds, by cannula, by os in an aqueous suspension of carboxymethylcellulose 2% w/v.

The animals are kept under observation for 14 days. In no animal of the group toxic symptoms appeared, even after administration of a 100 mg/Kg dose.

EXAMPLE F1

Test 1—experimental model in vivo with N-ethylmaleimide (NEM): study of the gastric tolerability of some drugs screened as precursors of the compounds of the invention.

The animals (rats, weight about 200 g) are distributed in the following groups (No. 10 animals for group):

A) Control Groups:
1° group: treatment: only carrier (aqueous suspension 1% w/v of carboxymethylcellulose, dose: 5 ml/Kg when the drug is administered by os, physiologic solution when by parenteral route),
2° group: treatment: carrier+NEM,
B) Groups Administered with Each Drug:
group I: treatment: carrier+drug,
group II: treatment: carrier+drug+NEM.

The drugs assayed in this experiment are the following (Table I): indomethacin, ambroxol, mesalamine, sodic alendronate, tacrine, omeprazol, misoprostol.

Indomethacin, ambroxol and alendronate are administered by os, mesalamine by intracolonic (rectal) route and tacrine, omeprazol, misoprostol by subcutaneous route.

The maximum tolerated dose, determined by administering each substance by the above said routes to the animals not treated with NEM, is reported in Table I. With higher doses than those reported in the Table, enteropathy, diarrhoea, depression, tremor and sedation have appeared in the animals.

In this experimental model, the animals are at first treated with NEM by subcutaneous injection at a dose of 25 mg/kg in physiologic solution. The drug is administered one hour later, in suspension in the carrier. Animals are sacrificed after 24 hours and evaluation of the damage to the gastrointestinal mucosa is made by counting the number of rats, inside each group, with lesions to the stomach at a visual inspection. The total number of said rats is then divided by the total number of rats of the group and multiplied by 100. The thus obtained percentages are reported in Table I. The Table shows that in the groups of rats treated with said drugs without NEM, no gastric lesions were detectable.

All the rats of group II (treated with NEM) showed gastric lesions after administration with the following drugs: indomethacin, ambroxol, mesalamine, sodic alendronate, tacrine. Said drugs therefore can be used in the synthesis of the products of the invention.

Omeprazol and misoprostol cannot instead be used, on the basis of the results provided in test 1, for preparing the products of the invention.

EXAMPLE F2

Test 2 (in vitro): inhibition of apoptosis (DNA fragmentation) induced in the endothelial cells by CIP in the presence of some drugs screened as precursors of the compounds of the invention.

The following precursor drugs (Table II): indomethacin, paracetamol, clopidogrel, salbutamol, ambroxol, sodic alendronate, diphylline, cetirizine, enalapril, nicotinamide, ampicilline, acyclovir, mesalamine, tacrine, simvastine, omeprazol have been tested.

Human endothelial cells of the umbilical vein are prepared according to a standard method. Fresh umbilical veins are filled with a collagenase solution 0.1% by weight and incubated at 37° C. for 5 minutes.

Subsequently the veins are perfused with the medium M 199 (GIBCO, Grand Island, N.Y.) pH 7.4 with 0.1% (weight/volume) of collagenase, added with 10% of bovine fetus serum (10 mcg/ml), sodium heparin (50 mcg/ml), thimidine (2.4 mcg/ml), glutamine (230 mcg/ml), penicillin (100

UI/ml), streptomycin (100 mcg/ml) and streptomycin B (0.125 mcg/ml). The cells are collected from the perfusate by centrifugation at 800 rpm and harvested in culture flasks T-75, pretreated with human fibronectin. Cells are then harvested in the same medium, added with bovine hypothalamic growth factor (100 ng/ml). When the cells of the primary cell culture (the cells directly removed from ex-vivo umbilical vein) form a single layer of confluent cells (about 8,000,000 cells/flask), harvesting is stopped and the layers are washed and trypsinized. The cellular suspensions are transferred into wells of a culture plate having 24 wells, half of said wells being added with the same culture medium containing the drug at a $10^{-4}$M concentration, and harvested in a thermostat at 37° C. at a constant moisture (90%), $CO_2$=5%. When the drug is not soluble in the culture medium, it is formerly dissolved in a small amount of dimethylsulphoxide. The maximum amount of dimethylsulphoxide which can be added to the culture medium is 0.5%. Only the cells coming from these first subcultures are used for the tests with cumene hydroperoxide (CIP). The cells are identified as endothelial cells by morphological examination and by the specific immunological reaction towards factor VIII; these cultures did never show contaminations from myocytes or fibroblasts.

Before starting the test, the cellular culture medium is removed and the cellular layers are carefully washed with a standard physiologic solution buffered with phosphate 0.1 M pH 7.0, at the temperature of 37° C. The content of each well is then incubated for one hour with a CIP suspension in the culture medium at a 5 mM concentration. Evaluation of the cellular damage (apoptosis) is carried out by determining the percent variation of the DNA fragmentation in the cultures containing the drug+CIP with respect to the controls treated with CIP only. Said % variation of DNA fragmentation is determined by evaluating the fluorescence variation by a BX60 Olympus microscope (Olympus Co., Roma) set at the wavelength of 405-450 nm, of the test samples with respect to the optical density of the controls. The fluorescence of each sample was determined on 5 replicates. Statistic evaluation has been made with t Student test (p<0.01).

Results are given in Table II and show that indomethacin, paracetamol, clopidogrel, salbutamol, sodic alendronate, diphylline, cetirizine, enalapril, nicotinamide, ampicilline, acyclovir, tacrine, omeprazol do not significantly inhibit apoptosis; these drugs can therefore be used for preparing the products of the invention.

On the contrary, ambroxol, mesalamine and simvastatine inhibit apoptosis. Therefore, on the basis of the results of test 2, these compounds could not be used for preparing the products of the invention.

EXAMPLE F3

Test 3—experimental in vivo model with N'-nitro-L-arginine-methyl ester (L-NAME): gastric tolerability (gastrointestinal damage incidence), hepatic (GPT dosage, glutamic-pyruvic transaminase) and cardiovascular (blood pressure) tolerability of some drugs screened as precursors of the compounds of the invention.

The experimental model adopted is according to J. Clin. Investigation 90, 278-281,1992.

The endothelial dysfunction is evaluated by determining the damage induced by L-NAME administration to the gastrointestinal mucosa, the hepatic damage (GPT increase), and the vascular endothelium or cardiovascular damage as blood hypertension.

The animals (rats, average weight 200 g) are divided in groups as herein below described. The group receiving L-NAME is treated for 4 weeks with said compound dissolved at the concentration of 400 mg/litre in drinking water. The following groups (No. 10 animals for group) are constituted:

A) Control Groups:
  1° group: treatment: only carrier (aqueous suspension 1% w/v of carboxymethylcellulose, dose: 5 ml/Kg when the drug is administered by os, physiologic solution when by parenteral route),
  2° group: treatment: carrier+L-NAME,
B) Groups Treated with the Drug:
  3° group: treatment: carrier+drug,
  4° group: treatment: carrier+drug+L-NAME.

The drugs used in the test are paracetamol, doxorubicine, simvastatine, omeprazol and misoprostol. Each drug is administered once a day for 4 weeks.

The maximum tolerated dose of the drug being administered to the animals is determined by evaluating, in a separate dose scaling up experiment on untreated animals, the appearance in the animals of symptoms such as enteropathy, diarrhoea, depression, tremor, sedation.

At the end of the four weeks, access to water is prevented, and after 24 hours, the animals are sacrificed.

One hour before the sacrifice blood pressure is determined and a blood pressure increase is taken as an indication of a damage being occurred to vascular endothelium.

The damage to the gastric mucosa is evaluated as previously mentioned in test 1 (ex. F1). The hepatic damage is determined by evaluation after the sacrifice of the glutamic-pyruvic transaminase (GPT increase).

The drug meets test 3 and it can therefore be used for preparing the compounds of the invention, when in the group of rats treated with L-NAME+drug+carrier, a higher hepatic damage (higher GPT values) and/or higher gastric damage and/or higher cardiovascular damage (higher blood pessure) are found in comparison with the group treated with the carrier only, or the group treated with carrier+drug, or the group treated with carrier+L-NAME.

The test results are reported in Table IV. The % gastric lesions have been determined as in Test 1. The % GPT and % blood pressure values are referred to the corresponding value found in the animals of the 1st group of the control groups. The average value of the blood pressure in this group was of 105±8 mmHg.

The results obtained show that paracetamol, doxorubicin and simvastatine cause hepatc damage and gastroenteropathy (GPT values and the gastric lesions are % higher compared both with the corresponding groups treated with the drug, in the absence of L-NAME, and with the controls treated with L-NAME).

These drugs can therefore be used for preparing the products of the invention.

Omeprazol and misoprostol should not instead be used, on the basis of this test, for preparing the products of the invention.

EXAMPLE F4

Test 4: inhibition of the radical production from DPPH of some substances to be used as precursors of B or B1 (ref. Formulas I and II of the invention)

The method is based on a colorimetric test in which DPPH (2,2-diphenyl-1-picryl-hydrazyl) is used as the compound-forming radicals (M.S. Nenseter et al., Atheroscler. Thromb. 15, 1338-1344, 1995).

Solutions in methanol of the tested substances at a final concentration 100 μM are initially prepared. 0.1 ml of each of these solutions are added to aliquots of 1 ml of a methanol solution 0.1 M of DPPH and then the final volume is brought to 1.5 ml. After having stored the solutions at room temperature away from light for 30 minutes, the absorbance at the wavelength of 517 nm is read. It is determined the absorbance decrease with respect to the absorbance of a solution containing the same concentration of DPPH.

The efficacy of the test compound to inhibit the production of radicals, or antiradical activity, is expressed by the following formula:

$$(1-A_S/A_C) \times 100$$

wherein $A_S$ and $A_C$ are, respectively, the absorbance values of the solution containing the test compound together+DPPH and of the solution containing only DPPH.

The compound meets test 4 if radical production inhibition, as above defined, is equal to or higher than 50%.

In Table V, the results obtained with the following substances are reported: N-acetylcisteine, cisteine, ferulic acid, (L)-carnosine, gentisic acid.

Table V shows that N-acetylcisteine, cisteine, ferulic acid, (L)-carnosine, gentisic acid meet test 4 since they inhibit the production of radicals formed from DPPH by more than 50%.

EXAMPLE F5

Antiinflammatory activity and gastric tolerability of the compounds according to the invention in comparison with the corresponding precursor drugs in conditions of endothelial dysfunction induced by L-NAME ($N^w$-nitro-L-arginine-methyl ester).

The experimental model of Edwards et al., J. Pathol. 134, 147-156, 1981 was followed.

Groups formed by 10 rats, having an average weight of 200 g, have been constituted. The groups have been treated with L-NAME dissolved in drinking water (400 mg/l) for two weeks, except one group which constituted the control group.

The drugs were administered by os, at the dose of 10 mg/Kg, in carrier carboxymethylcellulose 1% in water, 5 ml/Kg.

Thus, the groups, except the below-described control groups, were treated with the drug+L-NAME+carrier.

The following control groups were formed:
1° control group: treatment: carrier.
2° control group: treatment: carrier+L-NAME.

The drugs used in the experiment are the following: diclofenac and the corresponding thioester with (4-nitroxy)butyryl penicillamine (Ex. 26), piroxicam and the corresponding ester with the p-(4-nitroxy)butyryloxy-ferulic acid (Ex. 25), the acetylsalicylic acid and the corresponding thioester with N-acetyl-(4-nitroxy)butyrylcisteine (Ex. 24).

After two weeks from the beginning of the experiment, the animals were subjected to three consecutive injections of air by subcutaneous route, in the dorsal part of the animal, according to the following procedure:
first injection: 20 ml,
after three days from the first injection: 10 ml.
after 6 days from the first injection: the same amount of 10 ml.

The animals were then fasted until the following morning. One hour before the percutaneous injection with carrageiine (a ml of a 1% carragenine solution in water) in the inflammatory exudate, the treated animals received by os the carrier or one of the tested compounds dissolved or suspended in the carrier. The animals were sacrificed after 6 hours from the injection of the carragenine solution. The inflammatory exudate was collected and measured to evaluate the leucocyte infiltration.

In Table VI the antiinflammatory activity is expressed as % inhibition of the leucocyte infiltration with respect to the leucocyte infiltration value found in the animals treated with the carrier and pretreated with L-NAME, the % inhibition of the gastrointestinal damage was evaluated as previously described in Test 1 (ex. 1), and the % blood pressure was evaluated one hour before the sacrifice and referred to that of the 1st control group (treatment: carrier). In this group of animals the average pressure value was of 108±10 mmHg.

Table VI shows that the compounds of the invention are as active as the corresponding precursors in the antiinflammatory activity test, but in the confront of the latter they reduce the damage to the cardiovascular endothelium (lower % increase of blood pressure with respect to that of the corresponding precursor), and besides reduce, or do not give at all, gastric damage.

EXAMPLE F6

In a second apoptosis experiment indomethacin and the indomethacin thioester with N-acetyl-(4-nitroxy)butyryl cisteine (Ex. 3) according to the present invention were compared. The results are reported in Table III, and show that the compound of the invention inhibits, differently from the precursor, the apoptosis induced by cumene hydroperoxide (CIP).

EXAMPLE F7

Gastric tolerability of some drugs used as precursors and of the corresponding compounds according to the invention.

The test for gastrointestinal damage of Example F5 was repeated but omitting the pretreatment of animals with L-NAME. The tested drugs, thereof administered doses and results are reported in Table VII. From the Table it is drawn that gastropathy incidence is much lower in the groups treated with the compounds of the invention in the confront of the groups treated with the corresponding precursors.

EXAMPLE 27

Synthesis of (S)-N-acetyl-S-[[1-[5-(2,5-dihydro-5-oxo-3-furanyl)-3-methyl-2-benzofuranyl]ethyloxy)-4-oxo-butanoyl) cysteine (4-nitroxy)butyl Ester of Formula

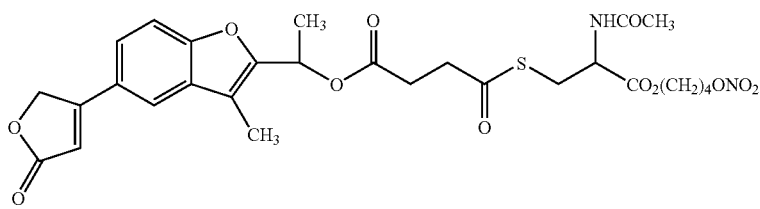

wherein the precursor is benfurodil hemisuccinate of formula (XXXI) and the precursor of 3 is N-acetylcysteine (formula CVIII)

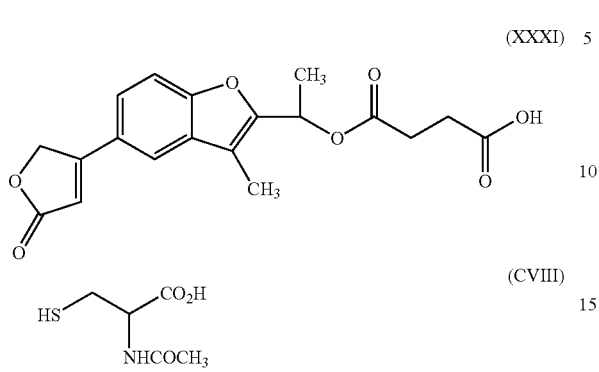

(XXXI)

(CVIII)

The compound is synthetized according to the process described in Example 4. Yield 25%.
Elementary analysis

| Calculated | C: 54.19% | H: 5.20% | N: 4.51% | S: 5.17% |
| Found | C: 54.25% | H: 5.22% | N: 4.47% | S: 5.15% |

EXAMPLE 28

Synthesis of (8S-cis)-10[(3-amino,2,3,6-tri-deoxy-α-L-lyxo-exo pyranosyl)oxy]-7,8,9,10-tetrahydro,6,8,11-trihydroxy-8-[[[3-methoxy-4-(4-nitroxybutanoyl)phenyl]-2-transpropenoyl-oxy]methyl-oxo]-1-methoxy-5,12-naphtacenedione of formula

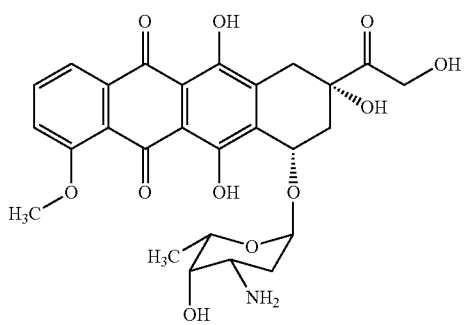

wherein the precursor is doxorubicin of formula (XXXII) and the precursor of B is ferulic acid of (formula DII)

(XXXII)

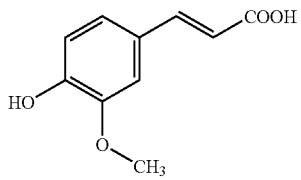

(DII)

The compound is synthetized according to the process described in Example 9. Yield 11%.
Elementary analysis

| Calculated | C: 57.88% | H: 4.98% | N: 3.29% |
| Found | C: 57.91% | H: 5.02% | N: 3.27% |

EXAMPLE F8

Example F1 was repeated with four groups of rats (each group of ten animals), all of them receiving NEM, and orally administered as follows:

a. control group: the vehicle formed of an aqueous suspension 1% w/v of carboxymethylcellulose, b. one group (group b—comparative) administered at the same time with 5 mg/Kg (0.014 mmoles/Kg) of indomethacin+2.3 mg/Kg (0.014 mmoles/Kg) of N-acetylcysteine in the same above vehicle,

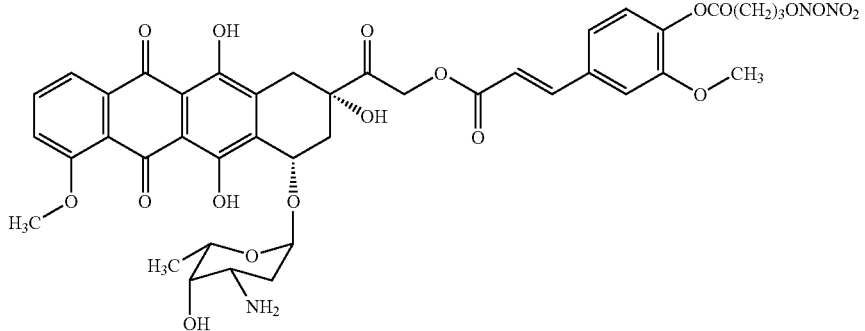

c. one group (group c—comparative) administered at the same time with 6.6 mg/Kg (0.014 mmoles/Kg) of indomethacin 4-(nitroxy)butyl ester, synthetized according to the method disclosed in WO 9-5/0983-1, +2.3 mg/Kg (0.014 mmoles/Kg) of N-acetylcysteine in the same above vehicle, d. one group (group d) administered with 8.7 mg/Kg (0.014 mmoles/Kg) of the indomethacin thioester with N-acetyl-(4-nitroxy)butyryl cisteine (ref. Ex. 3), in the above same vehicle.

The results are reported in Table VIII and show that the mixtures administered respectively to groups b and c (comparatives), differently from the compound of the invention administered to group d, were almost ineffective (group b) or much less effective (group c) in reducing gastric lesions.

TABLE I

Test 1: Gastric tolerability of drugs representative of the drug classes illustrated in the present invention in animals not treated or treated with NEM (oxidative stress conditions). The % incidence is calculated from the ratio between the number of animals found with gastric lesions and that total of the group.

| Compound | dose (mg/Kg)/ admin. route | Gastro-enteropathy (% incidence) without NEM | with NEM |
|---|---|---|---|
| carrier | | 0 | 0 |
| Indomethacin | 7.5/p.o. | 0 | 100 |
| Ambroxol | 25/p.o. | 0 | 80 |
| Mesalamine | 750/i.c. | 0 | 60 |
| Alendronate | 15/p.o. | 0 | 90 |
| Tacrine | 1/s.c. | 0 | 100 |
| Omeprazol | 30/s.c. | 0 | 0 |
| Misoprostol | 0.5/s.c. | 0 | 0 | p.o. = per os;
i.c. = by intracolonic route;
s.c. = by subcutaneous route.

TABLE II

Test 2: Inhibition of apoptosis (DNA fragmentation) induced by CIP in the endothelial cells in the presence of compounds representative of the drug classes illustrated in the present invention.

| Compound | Apoptosis % with respect to the controls treated only with CIP |
|---|---|
| Indomethacin | 95 |
| Paracetamol | 120 |
| Clopidogrel | 110 |
| Salbutamol | 90 |
| Ambroxol | 70 |
| Alendronate | 160 |
| Diphylline | 95 |
| Cetirizine | 115 |
| Enalapril | 80 |
| Nicotinamide | 98 |
| Ampicilline | 94 |
| Aciclovir | 95 |
| Mesalamine | 74 |
| Tacrine | 90 |
| Simvastatine | 72 |
| Omeprazol | 90 |

TABLE III

Test 2: comparison of the inhibition of apoptosis (DNA fragmentation), induced by CIP in endothelial cells in the presence of indomethacin and of a corresponding ester according to the present invention.

| Compound | Apoptosis % with respect to the controls treated only with CIP |
|---|---|
| Indomethacin (comp.) | 95 |
| Indomethacin thioester with N-acetyl-(4-nitroxy)butyryl cisteine (ref. Ex. 3) | 20 |

TABLE IV

Test 3: Gastric tolerability (gastrointestinal damage incidence), hepatic (GPT dosage, glutamic-pyruvic transaminase), and cardiovascular (blood pressure) of some compounds representative of the drug classes illustrated in the present invention in conditions of endothelial trouble induced by L-NAME.
The results relating to the blood pressure and GPT are expressed as % values with respect to those found in the animals treated with the only carrier, without L-Name.

| Compound | dose mg/Kg/ administ. route | Blood pressure % without L-NAME | with L-NAME | GPT % without L-NAME | with L-NAME | Gastroenteropathy % without L-NAME | with L-NAME |
|---|---|---|---|---|---|---|---|
| Carrier | | 100 | 152 | 100 | 155 | 0 | 30 |
| Paracetamol | 300/i.p. | 108 | 155 | 180 | 500 | 20 | 90 |
| Doxorubicine | 1/i.p. | 120 | 145 | 195 | 360 | 30 | 100 |
| Simvastatin | 50/p.o. | 85 | 148 | 122 | 220 | 0 | 60 |
| Omeprazol | 30/s.c. | 100 | 150 | 100 | 160 | 0 | 10 |
| Misoprostol | 0.5/s.c. | 100 | 142 | 100 | 160 | 0 | 5 |

TABLE V

Test 4: Screening of the effectiveness of the listed compounds in inhibiting radical production from DPPH.

| Compound | % inhibition radicals from DPPH |
|---|---|
| Solvent | 0 |
| N-acetylcisteine | 100 |
| Cisteine | 100 |
| Ferulic acid | 100 |
| (L)-carnosine | 80 |
| Gentisic acid | 80 |
| Penicillamine | 100 |

TABLE VI

Antiinflammatory activity (leucocyte infiltration with respect to the animals treated with carrier and pretreated with L-NAME), gastric tolerability and blood pressure (with respect to the animals not pretreated with L-NAME) of some drugs and of the corresponding compounds according to the present invention

| Compound | dose mg/Kg | Leucocyte infiltration % inhibition | Blood pressure % | Gastropathy % incidence |
|---|---|---|---|---|
| Carrier | — | — | 145 | 30 |
| Diclofenac (comp.) | 10 | 68 | 155 | 100 |
| Diclofenac thioester with (4-nitroxy)butyryl penicillamine (Ex. 26) | 10 | 70 | 115 | 20 |
| Piroxicam (comp.) | 10 | 78 | 145 | 100 |
| Piroxicam ester with p-(4-nitroxy)butyryloxy ferulic acid (Ex. 25) | 10 | 75 | 110 | 10 |
| Acetylsalicylic acid (comp.) | 50 | 60 | 160 | 100 |
| Thioester acetylsalicylic acid with N-acetyl-(4-nitroxy) butyryl cisteine (Ex. 24) | 50 | 55 | 110 | 0 |

TABLE VII

Test on gastric tolerability of the listed drugs and of the corresponding derivatives according to the present invention performed on rats not pretreated with L-NAME

| Compound | dose mg/Kg | Gastropathy % incidence |
|---|---|---|
| Carrier | — | — |
| Diclofenac | 20/p.o. | 70 |
| Diclofenac derivative Ex. 26 | 20/p.o. | 0 |
| Ambroxol | 100/p.o. | 60 |
| Ambroxol Derivative Ex. 9 | 100/p.o. | 10 |
| Alendronate | 100/p.o. | 90 |
| Alendronic acid Derivative Ex. 10 | 100/p.o. | 20 |
| Tacrine | 10/s.c. | 80 |
| Tacrine Derivative Ex. 17 | 10/s.c. | 20 |

What is claimed is:

1. A compound or a salt thereof having the following general formula (I):

A—B—C—N(O)$_2$   (I)

wherein:
A =R-T$_1$-, wherein
R is the radical of a drug having the formula R—T$_1$—Z or R—T$_1$—OZ, wherein
T$_1$ is (CO), O, S, N or NR$_{1C}$ wherein
R$_{1C}$ is H, C$_1$-C$_5$ alkyl or a free valance,
Z is H or C$_1$-C$_5$ alky; and
the drug having the formula R-T$_1$-Z or R-T$_1$-OZ is selected from the following classes:

anti-inflammatory drugs: acetylsalicylic acid, 5-aminoacetylsalicylic acid, carprofen, diclofenac sodium salt, diflunisal, etodolac, flufenamic acid, flunixin, flurbiprofen, ibuprofen, indomethacin, indoprofen, ketoprofen, ketorolac, lornoxicam, loxoprofen, meclofenamic acid, mefenamlc acid, meloxicam, mesalamine, naproxen, niflumic acid, olsalazine, piroxicam, salsalate, sulindac, suprofen, tenoxicam, tiaprofenic acid, tolfenamic acid, tolmetin, and zomepirac;

analgesic drugs: acetaminophen, acetylsalicylsallcylic acid, benoxaprofen, buprenorphine, butorphanol, capsaicin, diacereine, dihydrocodeine, ethylmorphine, eugenol, phenylbutazone, meptazinol, morphine, nalbuphine, pentazocine, thiorphan, tramadol, actarit;

bronchodilators drugs: albuterol, carbuterol, clenbuterol, dyphylline, etofylline, fenoterol, metaproterenol, pirbuterol, salmeterol, and terbutaline;

antihistaminic drugs: cetirizine, levocabastine, and terfenadine;

ACE-inhibitors: captopril, enalapril, lisinopril, ramipril;

beta blockers: alprenolol, atenolol, bupranolol, labetalol, metipranolol, metoprolol, pindolol, propranolol, timolol;

antithrombotic and vasoactive drugs: acetorfan, argatroban, clopidogrel, dalteparin, dipyridamole, enoxaparin, heparin, iloprost, midodrine, ozagrel, phenylpropanolamine, trifusal;

antidiabetic drugs: nicotinamide, tolrestat;

antiulcer drugs: cimetidine, omeprazole and pantoprazole;

antiviral drugs: acyclovir, famciclovir, ganciclovir, penciclovir, ribavirin, vidarabine, zidovudine;

B =T$_B$-X$_2$-T$_{BI}$-wherein
T$_B$ and T$_{BI}$ are equal or different,
T$_B$ is (CO) when T$_1$ is O, S, N, or NR$_{1C}$, wherein R$_{1C}$ is as above defined, or
T$_B$ is O, S, N, or NR$_{1C}$, wherein R$_{1C}$ is as above defined, when T$_1$ is (CO);
T$_{BI}$ is (CO), O, S, N, or NR$_{1C}$, wherein R$_{1C}$ is as above defined;
X$_2$ is a bivalent bridging group having the formula Z'-T$_B$-X$_2$-T$_{BI}$-Z'', in which Z', Z'' are independently H or OH, T$_B$, X$_2$, and T$_{BI}$ are as above defined, and Z'-$_B$-X$_2$-T$_{BI}$-Z'' is selected from the following aminoacids: L-carnosine (CI), penicillamine (CV), N-acetylpenicillamine (CVI), cysteine (CVII), N-acetylcysteine (CVIII):

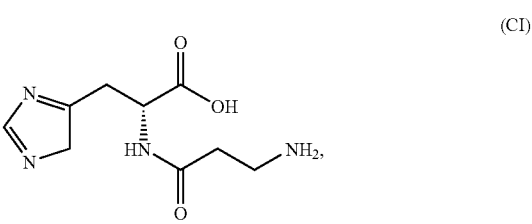

(CI)

-continued

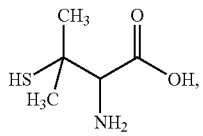
(CV)

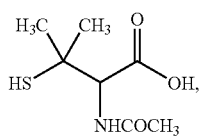
(CVI)

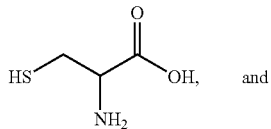
(CVII)

-continued

(CVIII)

C is a bivalent radical -$T_C$-Y— wherein
$T_C$ is (CO) when $T_{B1}$ is O, S, or $NR_{1C}$,
$T_C$ is O, S, or $NR_{1C}$ when $T_{B1}$ is (CO), $R_{1C}$ being as above defined,
Y is a linear or branched $C_1$-$C_{20}$ alkylenoxy group.

2. The compound or salt thereof according to claim 1, wherein Y is an $C_1$-$C_6$ linear or branched alkylenoxy group.

3. A pharmaceutical composition comprising a compound or salt according to claim 1 and a pharmaceutically acceptable carrier.

4. A method for treating oxidative stress dysfunction, the method comprising administering a therapeutically effective amount of the compound or salt according to claim 1 to a patient in need thereof.

* * * * *